US012796891B2

(12) United States Patent
Harada

(10) Patent No.: US 12,796,891 B2
(45) Date of Patent: Nov. 17, 2026

(54) CLOGGING DETERMINATION DEVICE FOR ENDOSCOPE PIPE LINE AND CLOGGING DETERMINATION METHOD FOR ENDOSCOPE PIPE LINE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 134 days.

(21) Appl. No.: 18/889,343

(22) Filed: Sep. 18, 2024

(65) Prior Publication Data

US 2025/0009205 A1 Jan. 9, 2025

Related U.S. Application Data

(63) Continuation of application No. PCT/JP2023/009249, filed on Mar. 10, 2023.

(30) Foreign Application Priority Data

Mar. 22, 2022 (JP) ................................ 2022-045703

(51) Int. Cl.
*A61B 1/00* (2006.01)
*A61B 1/015* (2006.01)

(52) U.S. Cl.
CPC ...... *A61B 1/00057* (2013.01); *A61B 1/00006* (2013.01); *A61B 1/015* (2013.01)

(58) Field of Classification Search
CPC . A61B 1/00057; A61B 1/00006; A61B 1/015; A61B 1/00055; A61B 1/00068;
(Continued)

(56) References Cited

U.S. PATENT DOCUMENTS 7,901,349 B2 3/2011 Feld et al.
8,758,519 B2 6/2014 Waldmann et al.
(Continued)

FOREIGN PATENT DOCUMENTS

JP 2009514611 4/2009
JP 2009226193 10/2009
(Continued)

OTHER PUBLICATIONS

"International Search Report (Form PCT/ISA/210) of PCT/JP2023/009249", mailed on May 23, 2023, with English translation thereof, pp. 1-4.

(Continued)

*Primary Examiner* — Timothy J Neal
(74) *Attorney, Agent, or Firm* — JCIPRNET

(57) ABSTRACT

A washing adapter to be inserted into a space portion of a cylinder, includes a valve member attached to a shaft part, and the valve member is switchable between a contact state of being in contact with an interior wall of the cylinder and a spaced state of being spaced apart from the interior wall. A clogging determination unit switches the valve member between the contact state and the spaced state. The valve member brings at least one pipe line of an air feeding pipe line, an air supply pipe line, a water feeding pipe line, or a water supply pipe line into a state of being out of communication with the other pipe lines in the space portion in the contact state, and brings all of the pipe lines into a state of being in communication with the other pipe lines in the space portion in the spaced state.

15 Claims, 26 Drawing Sheets

(58) Field of Classification Search
CPC . A61B 1/012; A61B 1/00094; A61B 1/00091; A61B 1/00137; A61M 16/0463; A61M 1/84; F16K 1/12; F16K 1/123
See application file for complete search history.

(56) References Cited

U.S. PATENT DOCUMENTS

| | | | | |
|---|---|---|---|---|
| 9,492,066 | B2 | 11/2016 | Iwasaki | |
| 9,565,995 | B2 | 2/2017 | Nguyen et al. | |
| 10,188,276 | B2 | 1/2019 | Iwasaki | |
| 10,582,984 | B2 | 3/2020 | Nguyen et al. | |
| 2007/0185385 | A1 | 8/2007 | Noguchi et al. | |
| 2009/0220377 | A1 | 9/2009 | Hasegawa et al. | |
| 2014/0066839 | A1 | 3/2014 | Torisawa et al. | |
| 2016/0022127 | A1* | 1/2016 | Iwasaki | B08B 9/053 15/3.5 |

FOREIGN PATENT DOCUMENTS

| | | |
|---|---|---|
| JP | 2010029467 | 2/2010 |
| JP | 2011521751 | 7/2011 |
| JP | 2012505032 | 3/2012 |
| JP | 2014050532 | 3/2014 |
| JP | 2014050533 | 3/2014 |
| WO | 2006001336 | 1/2006 |
| WO | 2015125347 | 8/2015 |

OTHER PUBLICATIONS

"Written Opinion of the International Searching Authority (Form PCT/ISA/237) of PCT/JP2023/009249", mailed on May 23, 2023, with English translation thereof, pp. 1-6.

* cited by examiner

CLOGGING DETERMINATION DEVICE FOR ENDOSCOPE PIPE LINE AND CLOGGING DETERMINATION METHOD FOR ENDOSCOPE PIPE LINE

CROSS-REFERENCE TO RELATED APPLICATIONS

The present application is a Continuation of PCT International Application No. PCT/JP2023/009249 filed on Mar. 10, 2023 claiming priority under 35 U.S.C § 119(a) to Japanese Patent Application No. 2022-045703 filed on Mar. 22, 2022. Each of the above applications is hereby expressly incorporated by reference, in its entirety, into the present application.

BACKGROUND OF THE INVENTION

1. Field of the Invention

The present invention relates to a clogging determination device and a clogging determination method for determining clogging of an endoscope pipe line.

2. Description of the Related Art

An endoscope includes a plurality of pipe lines used for guiding a gas, a liquid, and a treatment tool. In a case in which such an endoscope is washed (including disinfection, the same applies below) by an endoscope washing device, the pipe line also needs to be washed. In order to correctly wash the pipe line, it is necessary to detect (determine) in advance a clogged (blocked) state of the pipe line before washing the pipe line.

JP2011-521751A discloses a technology of detecting a clogged state of a pipe line by measuring a maximum value and a minimum value of a pressure by using a pressure pulse.

JP2009-514611A discloses a technology of detecting a clogged state of a pipe line by monitoring a time required for a back pressure of a pressurized fluid to drop to a predetermined value.

Meanwhile, among the pipe lines of the endoscope, for example, a pipe line for supplying air and water toward an observation window is branched from one pipe line (so-called air/water supply pipe line) into two pipe lines (so-called air supply pipe line and water supply pipe line) and communicates with a space portion of a cylinder, in terms of a function of switching between air and water via a button operation. In the pipe line having such a branch structure (hereinafter, referred to as a branch pipe line), for example, even in a case in which the air supply pipe line is clogged, the pressure fluctuation is less likely to occur in a case in which the pressurized fluid flows out from the water supply pipe line. Therefore, in the technologies disclosed in JP2011-521751A and JP2009-514611A in which the clogged state is detected based on the pressure fluctuation, there is a problem in that it is difficult to accurately determine the clogged state of the branch pipe line.

JP2012-505032A discloses a separator that solves the problems of JP2011-521751A and JP2009-514611A. The separator has a function of partitioning a space portion of a cylinder into a flow passage of an air supply pipe line and a flow passage of a water supply pipe line. By using the separator, it is possible to determine a clogged state of each pipe line of the air supply pipe line and the water supply pipe line. However, since the separator has a configuration in which an inside of the cylinder is partitioned by a sealing member such as an O-ring, there is a problem in that an interior wall part of the cylinder in contact with the sealing member is not washed.

WO2015/125347A discloses a separator that can solve the problem of JP2012-505032A. The separator includes an elastic member. The elastic member is in a spaced state of being spaced apart from an interior wall of a cylinder in a case of being open (that is, in a case in which clogging does not occur), but is switched to a contact state in which the elastic member is increased in diameter and is in contact with the interior wall of the cylinder due to an internal pressure difference between an air supply pipe line and a water supply pipe line generated in a case of clogging. According to WO2015/125347A, an interior wall part of the cylinder in contact with the elastic member can be washed in a case of being open.

SUMMARY OF THE INVENTION

However, the separator of WO2015/125347A has the following problem. That is, since the diameters and the lengths of the pipe lines vary depending on a model of the endoscope and the pipe line resistances are different from each other, there is a problem in that it is difficult to set the switching between the spaced state and the contact state of the elastic member (hereinafter, referred to as a valve member) with respect to the interior wall of the cylinder. That is, the valve member of WO2015/125347A is in the spaced state in advance, and is switched to the contact state in a case in which the pipe line is clogged. Therefore, it is necessary to set a boundary value (threshold value) at which the valve member is switched between the spaced state and the contact state, but the threshold value is different for each model because the pipe line resistance of the endoscope is different for each model. As a result, in the technology of WO2015/125347A, there is a problem in that the separator of the specification corresponding to each model should be prepared, which is very time-consuming.

In a case in which a socket is washed at the same time as the pipe line while a washing solution is leaked from the socket of the pipe line (for example, see JP5165479B), it is more difficult to maintain the pressure in the pipe line in a balanced state. Therefore, the valve member may be biased to one side even in a case in which the pipe line is in an open state (that is, in a state in which no clogging has occurred in the pipe line), and in this case, there is a problem in that the clogging of the pipe line is erroneously determined. In addition, in the technology of separating the two pipe lines using the internal pressure difference as in WO2015/125347A, there is also a problem in that, even in a case in which the clogging has occurred in the pipe line (air/water supply pipe line) on a distal end side on which the two pipe lines are combined, the internal pressure difference does not occur, so that the clogging in the air/water supply pipe line cannot be detected.

Therefore, there is a demand for the development of a clogging determination device that can reliably wash the interior wall of the cylinder (space portion configuration member), and can detect clogging even in a case in which the clogging has occurred in any pipe line in a pipe line group including a plurality of pipe lines.

The present invention has been made in view of such circumstances, and an object of the present invention is to provide a clogging determination device for an endoscope pipe line and a clogging determination method for an endoscope pipe line with which it is possible to achieve both improvement in washing performance of an interior wall of a space portion configuration member and improvement in pipe line clogging detection performance.

In order to achieve the object of the present invention, an aspect of the present invention relates to a clogging determination device for an endoscope pipe line, the clogging determination device determining clogging of an endoscope pipe line including a pipe line group including four or more pipe lines, and a space portion configuration member formed with a space portion communicating with the pipe line group, the clogging determination device comprising: an adapter that is attachable to and detachable from the space portion, in which the adapter includes a shaft part that is inserted and disposed into the space portion, and a valve member that is attached to the shaft part, that is switchable between a contact state of being in contact with an interior wall of the space portion configuration member and a spaced state of being spaced apart from the interior wall, that brings at least one of the four or more pipe lines into a state of being out of communication with the other pipe lines in the space portion in the contact state, and that brings all of the four or more pipe lines into a state of being in communication with each other in the space portion in the spaced state, and a switching unit that switches the valve member between the contact state and the spaced state is provided.

According to the aspect of the present invention, it is preferable that the pipe line group includes a first pipe line, a second pipe line, a third pipe line, and a fourth pipe line, and the third pipe line and the fourth pipe line are combined with each other on a side opposite to the space portion, and the valve member brings at least one of the first pipe line, the second pipe line, the third pipe line, or the fourth pipe line into a state of being out of communication with the other pipe lines in the space portion in the contact state, and brings all of the first to fourth pipe lines into a state of being in communication with each other in the space portion in the spaced state.

According to the aspect of the present invention, it is preferable that the switching unit switches the valve member between the contact state and the spaced state at least once in a case in which the pipe line group is washed with a fluid supplied from some pipe lines of the pipe line group.

According to the aspect of the present invention, it is preferable that the switching unit switches the valve member between the contact state and the spaced state by changing a supply condition of a fluid supplied from some pipe lines of the pipe line group to the space portion.

According to the aspect of the present invention, it is preferable that the supply condition is a pressure or a flow rate of the fluid supplied into the space portion.

According to the aspect of the present invention, it is preferable that the valve member is formed by an elastic valve that is elastically contactable with the interior wall of the space portion configuration member.

According to the aspect of the present invention, it is preferable that the space portion includes a first flow passage and a second flow passage, the first flow passage and the second flow passage are in communication with each other in the spaced state, and the first flow passage and the second flow passage are out of communication with each other in the contact state, and the valve member is formed by a check valve that is in the contact state in a case in which one pressure of a pressure in the first flow passage or a pressure in the second flow passage is higher than the other pressure, and that is in the spaced state in a case in which the one pressure is lower than the other pressure.

According to the aspect of the present invention, it is preferable that the valve member is a tubular flexible member that covers an outer periphery of the shaft part, one end part of both end parts of the flexible member in an axial direction of the shaft part is a fixing part that is fixed to the shaft part, and the other end part is a movable part that is movable along the axial direction of the shaft part, and the flexible member is decreased in diameter and is in the spaced state in a case in which the movable part is located at a restriction position at which movement in a direction away from the fixing part is restricted, and the flexible member is increased in diameter and is in the contact state in a case in which the movable part is located at a position close to the fixing part with respect to the restriction position.

According to the aspect of the present invention, it is preferable that the valve member includes an abutting member that is configured to abut on an abutting target part provided in the space portion, and a biasing member that biases the abutting member in a direction of abutting on the abutting target part, the abutting member abuts on the abutting target part via the biasing member and is in the contact state in a case in which one pressure of the pressure in the first flow passage or the pressure in the second flow passage is higher than the other pressure, and the abutting member is spaced apart from the abutting target part against a biasing force of the biasing member and is in the spaced state in a case in which the one pressure is lower than the other pressure.

According to the aspect of the present invention, it is preferable that the space portion includes a first flow passage and a second flow passage, the first flow passage and the second flow passage are in communication with each other in the spaced state, and the first flow passage and the second flow passage are out of communication with each other in the contact state, and the valve member is in the contact state in a case in which a pressure difference between the first flow passage and the second flow passage is smaller than a threshold pressure difference, and is in the spaced state in a case in which the pressure difference is larger than the threshold pressure difference.

According to the aspect of the present invention, it is preferable that the valve member has a tapered part in which a thickness of a cross section orthogonal to an axial direction of the shaft part is smaller as a distance to the interior wall of the space portion configuration member is smaller.

According to the aspect of the present invention, it is preferable that the valve member is formed by a temperature deformable member that is deformable between the contact state and the spaced state according to a temperature change.

According to the aspect of the present invention, it is preferable that the switching unit changes a temperature of a fluid supplied into the space portion to deform the temperature deformable member between the contact state and the spaced state.

According to the aspect of the present invention, it is preferable that the switching unit brings the temperature deformable member into the contact state by setting a temperature applied to the temperature deformable member to be equal to or higher than a deformable temperature at which the temperature deformable member is deformable, and brings the temperature deformable member into the spaced state by setting the temperature of the temperature deformable member to be lower than the deformable temperature.

In order to achieve the object of the present invention, another aspect of the present invention relates to a clogging determination method for an endoscope pipe line, the clogging determination method being for determining clogging of an endoscope pipe line including a pipe line group including four or more pipe lines, and a space portion configuration member formed with a space portion communicating with the pipe line group, the clogging determination method comprising: a setting step of setting a pipe line route by switching a valve member disposed in the space portion between a contact state of being in contact with an interior wall of the space portion configuration member and a spaced state of being spaced apart from the interior wall, to perform selectively switching between a state in which at least one of the four or more pipe lines is out of communication with the other pipe lines in the space portion and a state in which all of the four or more pipe lines are in communication with each other in the space portion; a measurement step of measuring a back pressure of a fluid by supplying the fluid into the other pipe lines; a comparison step of comparing the measured back pressure with a clogging determination threshold value; and a determination step of determining whether or not the clogging has occurred.

According to the aspect of the present invention, it is preferable that the pipe line group includes a first pipe line, a second pipe line, a third pipe line, and a fourth pipe line, and the third pipe line and the fourth pipe line are combined with each other on a side opposite to the space portion, and in the setting step, at least one of the first pipe line, the second pipe line, the third pipe line, or the fourth pipe line is brought into a state of being out of communication with the other pipe lines in the space portion in the contact state, and all of the first to fourth pipe lines are brought into a state of being in communication with each other in the spaced state.

According to the aspect of the present invention, it is preferable that the clogging determination method for an endoscope pipe line further comprises a filling step of filling the other pipe lines with the fluid between the setting step and the determination step.

According to the aspect of the present invention, it is preferable that, in the setting step, the valve member is switched between the contact state and the spaced state by changing a pressure or a flow rate of the fluid supplied into the space portion.

According to the aspect of the present invention, it is preferable that, in the setting step, the valve member is switched between the contact state and the spaced state by changing a temperature of the fluid supplied into the space portion.

According to the aspects of the present invention, it is possible to achieve both the improvement in the washing performance of the interior wall of the space portion configuration member and the improvement in the pipe line clogging detection performance.

DESCRIPTION OF THE PREFERRED EMBODIMENTS

Hereinafter, a clogging determination device for an endoscope pipe line and a clogging determination method for an endoscope pipe line according to embodiments of the present invention will be described with reference to the accompanying drawings.

Figure 1:
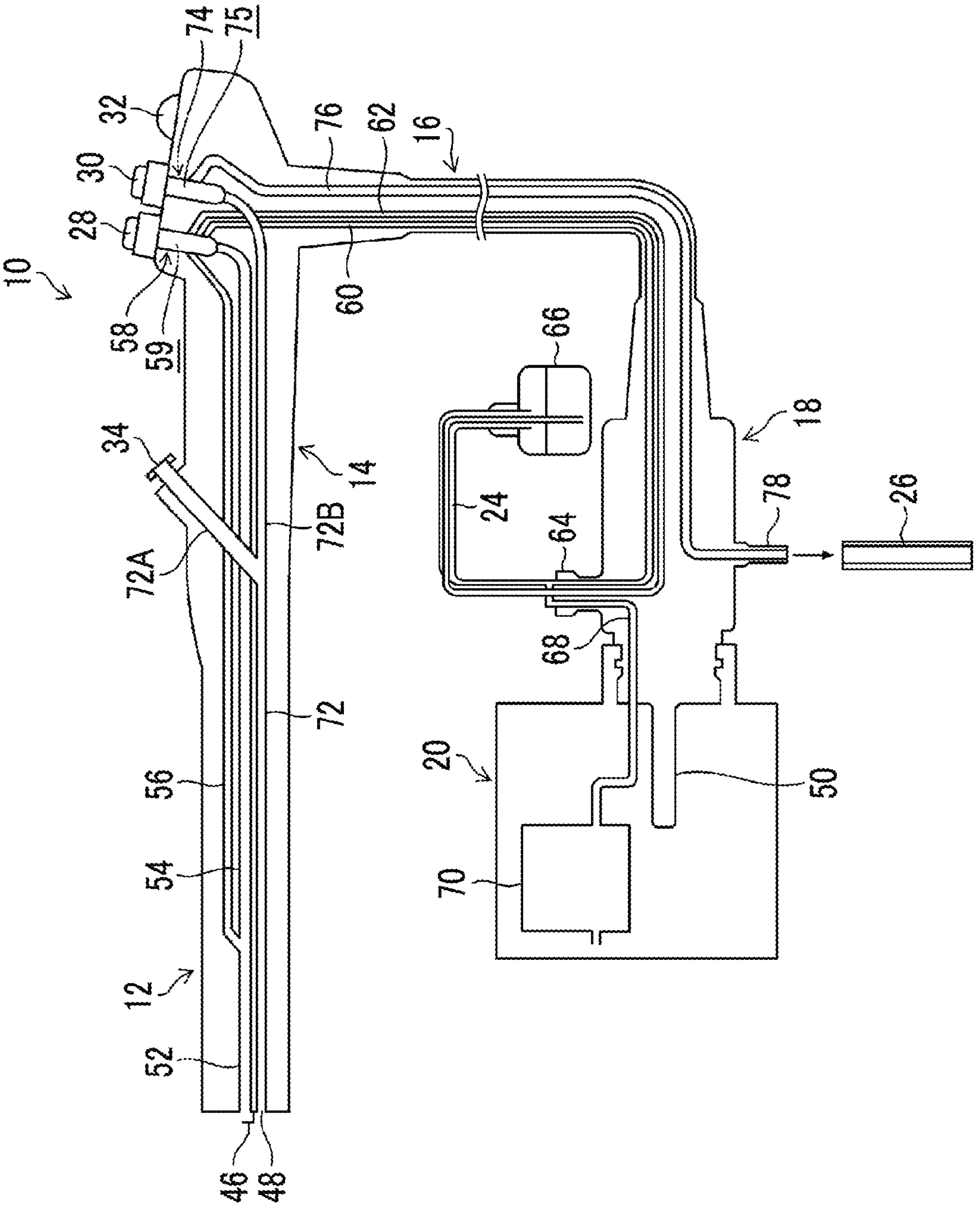
FIG. 1 is an overall view of an endoscope to be washed by an endoscope washing device according to an embodiment.

FIG. 1 is an overall view of an endoscope 10, and in particular, is an explanatory diagram schematically showing a configuration of an endoscope pipe line provided in the endoscope 10. A clogged state of the endoscope pipe line is determined by a clogging determination device 200 (see FIG. 5) according to the embodiment. First, a configuration of the endoscope 10 will be described with reference to FIG. 1.

As shown in FIG. 1, the endoscope 10 comprises an insertion part 12 to be inserted into a lumen of a patient, for example, into a digestive tract such as a stomach or a large intestine, and a hand-side operating part 14 that is installed consecutively with the insertion part 12. A universal cable 16 is connected to the hand-side operating part 14, and an LG connector 18 is provided at a distal end of the universal cable 16. By connecting the LG connector 18 to a light source device 20, illumination light is transmitted to illumination windows 22 and 22 (see FIG. 2). In addition, the LG connector 18 includes an electrical connector (not shown), and the electrical connector is attachably and detachably connected to a processor (not shown). It should be noted that a pipe line 24 for air/water supply and a tube 26 for suction are connected to the LG connector 18.

An air/water supply button 28, a suction button 30, and a shutter button 32 are installed adjacent to the hand-side operating part 14, and a pair of angle knobs (not shown) and a forceps insertion port 34 are provided in the hand-side operating part 14.

Figure 2:
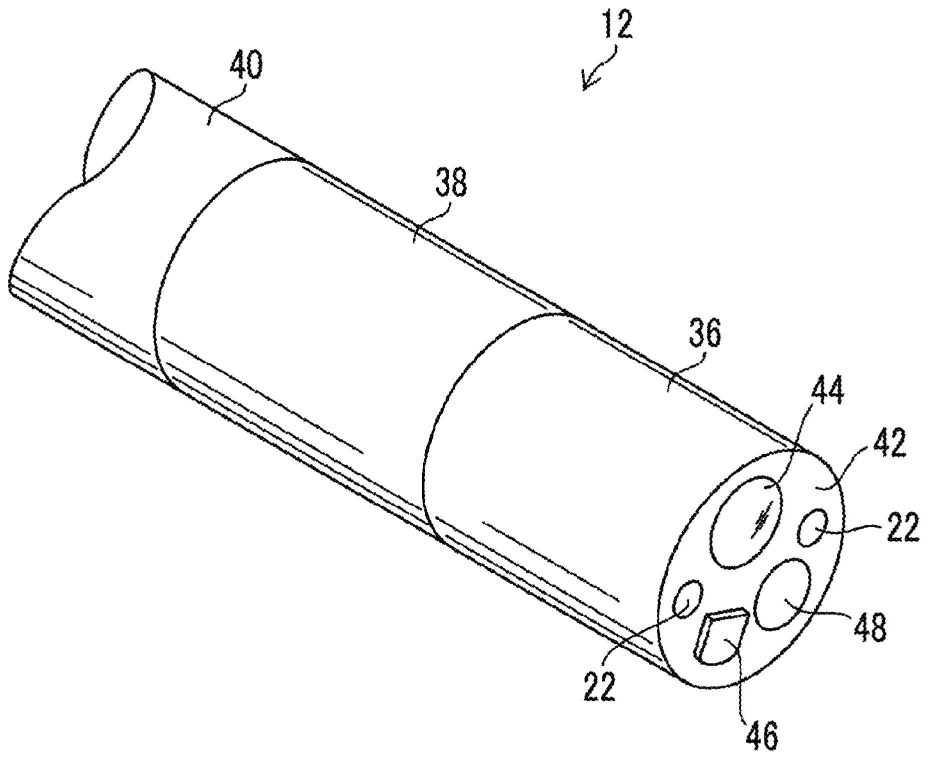
FIG. 2 is a main part perspective view showing a distal end side of an insertion part of the endoscope.

FIG. 2 is a main part perspective view showing a distal end side of the insertion part 12. As shown in FIG. 2, the insertion part 12 has a distal end part 36, a bendable part 38, and a soft part 40, and the bendable part 38 is bent remotely by rotationally moving the angle knobs provided in the hand-side operating part 14 (see FIG. 1). Accordingly, a distal end surface 42 of the distal end part 36 can be directed in a desired direction.

An observation window 44, the illumination windows 22 and 22, an air/water supply nozzle 46, and a forceps port 48 are provided on the distal end surface 42 of the distal end part 36. An imaging element (not shown) is disposed behind (base end side) the observation window 44, and a signal cable is connected to a substrate that supports the imaging element. The signal cable is inserted into the insertion part 12, the hand-side operating part 14, and the universal cable 16 of FIG. 1, is projected to the electrical connector, and is connected to the processor. Therefore, an observation image taken in from the observation window 44 of FIG. 2 is formed on a light-receiving surface of the imaging element and converted into an electrical signal, and this electrical signal is output to the processor via the signal cable and converted into a video signal. As a result, the observation image is displayed on a monitor (not shown) connected to the processor. It should be noted that a charge coupled device (CCD) image sensor or a complementary metal oxide semiconductor (CMOS) image sensor is used as the imaging element.

An emission end of a light guide (not shown) is disposed behind (base end side) the illumination windows 22 and 22. The light guide is inserted into the insertion part 12, the hand-side operating part 14, and the universal cable 16 of FIG. 1. Then, the incidence end of the light guide is connected to a light guide rod 50 of the LG connector 18. Therefore, by connecting the light guide rod 50 to the light source device 20, the illumination light emitted from the light source device 20 is transmitted to the illumination windows 22 and 22 via the light guide, and is emitted from the illumination windows 22 and 22. The schematic configuration of the endoscope 10 is as described above.

Next, the configuration of the endoscope pipe line of the endoscope 10 will be described.

As shown in FIG. 1, an air/water supply pipe line 52 is inserted into the insertion part 12 of the endoscope 10, and the air/water supply nozzle 46 is connected to an opening of the air/water supply pipe line 52 on the distal end side. The base end side of the air/water supply pipe line 52 is branched into an air supply pipe line 54 and a water supply pipe line 56, and the base end sides of these pipe lines communicate with a space portion 59 of a cylinder 58 for air/water supply provided in the hand-side operating part 14. That is, one end side of each of the air supply pipe line 54 and the water supply pipe line 56 communicates with the space portion 59 of the cylinder 58, and the other end side (opposite side to the space portion 59) of the air supply pipe line 54 and the water supply pipe line 56 is combined and connected to the air/water supply pipe line 52. The air supply pipe line 54 of the present example is an example of a third pipe line according to the embodiment of the present invention, and the water supply pipe line 56 of the present example is an example of a fourth pipe line according to the embodiment of the present invention. In addition, the cylinder 58 of the present example is an example of a space portion configuration member according to the embodiment of the present invention.

In addition, the distal end side of each of an air feeding pipe line 60 and a water feeding pipe line 62 communicates with the space portion 59 of the cylinder 58, and the air/water supply button 28 is attachably and detachably attached to the inside of the cylinder 58. In a state in which the air/water supply button 28 protrudes, the air supply pipe line 54 and the air feeding pipe line 60 communicate with each other via the space portion 59 of the cylinder 58, and by performing the pressing operation of the air/water supply button 28, the water supply pipe line 56 and the water feeding pipe line 62 communicate with each other via the space portion 59 of the cylinder 58. A ventilation hole (not shown) is formed in the air/water supply button 28, and the air feeding pipe line 60 communicates with outside air via the ventilation hole. The air feeding pipe line 60 of the present example is an example of a first pipe line according to the embodiment of the present invention, and the water feeding pipe line 62 of the present example is an example of a second pipe line according to the embodiment of the present invention.

The air feeding pipe line 60 and the water feeding pipe line 62 are inserted into the universal cable 16 and are projected toward a water supply connector 64 of the LG connector 18. The pipe line 24 is attachably and detachably connected to the water supply connector 64, and a distal end of the pipe line 24 is connected to a water storage tank 66. The water feeding pipe line 62 communicates below a liquid level of the water storage tank 66, and the air feeding pipe line 60 communicates above the liquid level.

An air pipe line 68 is connected to the water supply connector 64, and the air pipe line 68 communicates with the air feeding pipe line 60. In addition, the air pipe line 68 communicates with an air pump 70 in the light source device 20 by connecting the LG connector 18 to the light source device 20. Therefore, in a case in which the air pump 70 is driven to supply air, the air is supplied into the air feeding pipe line 60 through the air pipe line 68. The air is released to the outside through the ventilation hole (not shown) of the air/water supply button 28 during the non-operation of the air/water supply button 28, but the air in the air feeding pipe line 60 is supplied into the air supply pipe line 54 and the air is jetted from the air/water supply nozzle 46 by blocking the ventilation hole by means of an operator. In addition, in a case in which the pressing operation of the air/water supply button 28 is performed, the air feeding pipe line 60 and the air supply pipe line 54 are in a state of being out of communication with each other, so that the air supplied into the air pipe line 68 is supplied above the liquid level of the water storage tank 66. As a result, the internal pressure of the water storage tank 66 is increased, and water is fed into the water feeding pipe line 62. Then, water is jetted from the air/water supply nozzle 46 through the air/water supply pipe line 52 from the water supply pipe line 56. In this way, air or water is jetted from the air/water supply nozzle 46, and the observation window 44 is washed by blowing air or water to the observation window 44.

As shown in FIG. 1, a forceps pipe line 72 is inserted into the insertion part 12 of the endoscope 10, and a forceps port 48 is opened on the distal end side of the forceps pipe line 72. The base end side of the forceps pipe line 72 is branched into two pipe lines 72A and 72B, and the base end side of one pipe line 72A communicates with the forceps insertion port 34. Therefore, in a case in which the treatment tool such as the forceps is inserted from the forceps insertion port 34, the treatment tool can be led out from the forceps port 48 via the forceps pipe line 72. In addition, the base end side of the other pipe line 72B communicates with a space portion 75 of a cylinder 74 for suction.

A distal end side of a suction pipe line 76 communicates with the space portion 75 of the cylinder 74, and the suction button 30 is attachably and detachably attached to the cylinder 74. In a state in which the suction button 30 protrudes, the suction pipe line 76 communicates with the outside air, and the suction pipe line 76 and the forceps pipe line 72 communicate with each other via the space portion 75 of the cylinder 74 and the pipe line 72B by performing the pressing operation of the suction button 30.

The suction pipe line 76 is projected to a suction connector 78 of the LG connector 18, and a suction device (not shown) is connected to the suction connector 78 via a tube 26. Therefore, in a case in which the pressing operation of the suction button 30 is performed in a state in which the suction device is driven, a lesion part or the like can be suctioned through the forceps pipe line 72 from the forceps port 48.

Figure 3:
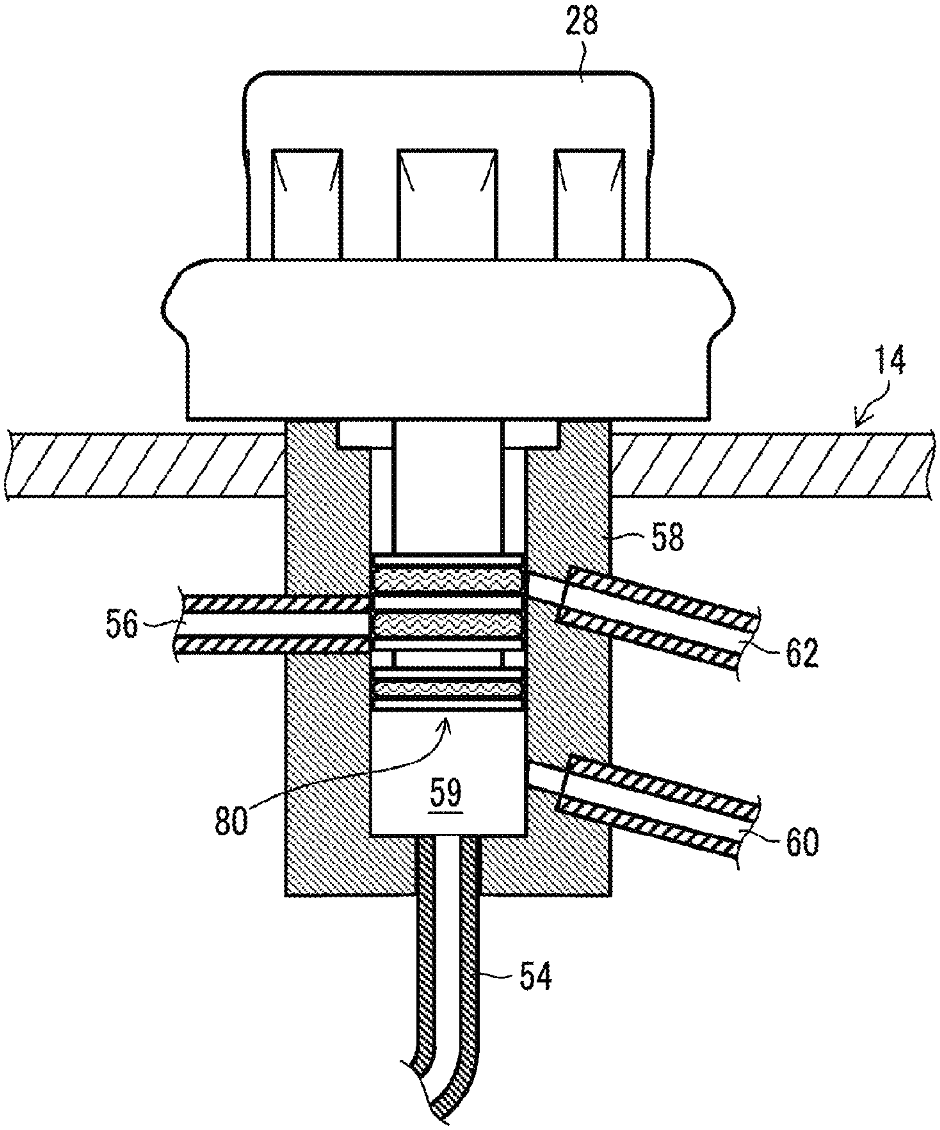
FIG. 3 is a cross-sectional view of a cylinder of an air/water supply system shown in FIG. 1.

FIG. 3 is a cross-sectional view showing an example of the cylinder 58 shown in FIG. 1. As shown in FIG. 3, the cylinder 58 is fixed to the hand-side operating part 14. The cylinder 58 is formed in a cylindrical shape in which one end is open and the other end has a bottom. A valve member 80 such as an O-ring, which is a component of the air/water supply button 28, is disposed slidably in an axial direction of the cylinder 58 in the space portion 59 of the cylinder 58. In a state before the pressing operation of the air/water supply button 28 shown in FIG. 3, the air feeding pipe line 60 and the air supply pipe line 54 communicate with each other via the space portion 59. Then, by moving the valve member 80 via the pressing operation of the air/water supply button 28, the water feeding pipe line 62 communicates with the water supply pipe line 56 through the space portion 59. It should be noted that, although not shown, a valve member that is also a component of the suction button 30 is similarly disposed slidably in the axial direction of the cylinder 74 in the cylinder 74. The suction pipe line 76 and the forceps pipe line 72 communicate with each other through the space portion 75 of the cylinder 74 and the pipe line 72B by moving the valve member by performing the pressing operation of the suction button 30.

The endoscope 10 configured as described above is configured such that the air/water supply button 28 can be removed from the cylinder 58 in order to determine a clogged state of a pipe line group (hereinafter, referred to as a branch pipe line A (not shown in the drawing)) including a plurality of pipe lines (air feeding pipe line 60, water feeding pipe line 62, cylinder 58, air supply pipe line 54, water supply pipe line 56, and air/water supply pipe line 52) constituting an air/water supply system, and to perform the washing. Similarly, the suction button 30 can also be removed from the cylinder 74 in order to determine the clogged state of the pipe line group (hereinafter, referred to as a suction system pipe line C (not shown in the drawing)) including a plurality of pipe lines (suction pipe line 76, cylinder 74, pipe line 72B, pipe line 72A, and forceps pipe line 72) constituting the suction system, and to perform the washing. In a case in which the clogged state of the branch pipe line A is determined and the washing is performed, for example, a washing adapter 100 (see FIG. 4) is attachably and detachably mounted in the cylinder 58 instead of the air/water supply button 28.

Figure 4:
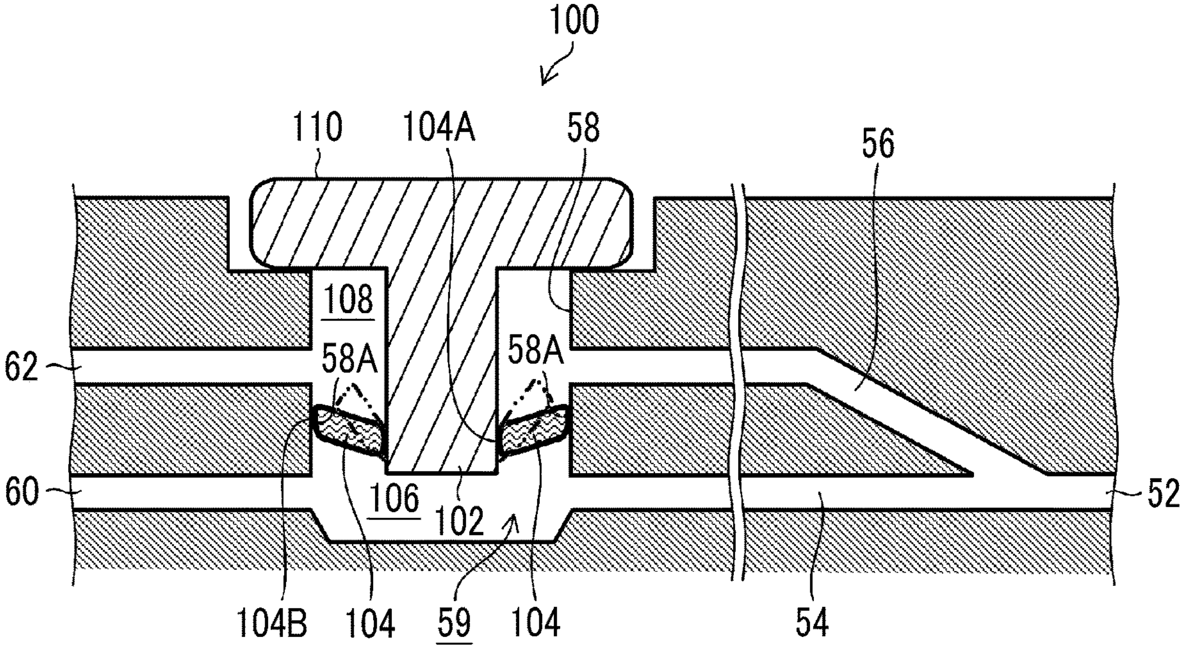
FIG. 4 is a cross-sectional view of a washing adapter mounted in a cylinder.

FIG. 4 is a cross-sectional view of the washing adapter 100 mounted on the cylinder 58. It should be noted that, in FIG. 4, another configuration including the cylinder 58 is schematically shown. The washing adapter 100 is an example of a washing adapter according to the embodiment of the present invention. As will be described below, the washing adapter 100 of the present example has a function of selectively switching between a state in which at least one of the four pipe lines (air feeding pipe line 60, water feeding pipe line 62, air supply pipe line 54, and water supply pipe line 56) is out of communication with the other pipe lines in the space portion 59 and a state in which all of the four pipe lines are in communication with each other in the space portion 59. The washing adapter 100 is also referred to as a so-called "separator".

As shown in FIG. 4, the washing adapter 100 includes a shaft part 102 that is inserted and disposed into the space portion 59 of the cylinder 58, and a valve member 104 that is attached to the shaft part 102 and is switchable between a contact state (solid line) of being in contact with the interior wall of the cylinder 58 and a spaced state (two-point chain line) of being spaced apart from the interior wall of the cylinder 58. In a case in which the valve member 104 is in the contact state, the space portion 59 of the cylinder 58 is separated into two flow passages (flow passage 106 and flow passage 108) interposing the valve member 104. As a result, the air feeding pipe line 60 and the air supply pipe line 54 communicate with each other via the flow passage 106, and the water feeding pipe line 62 and the water supply pipe line 56 communicate with each other via the flow passage 108. That is, in a case in which the valve member 104 is in the contact state, two pipe lines (air feeding pipe line 60 and air supply pipe line 54) of the four pipe lines (air feeding pipe line 60, water feeding pipe line 62, air supply pipe line 54, and water supply pipe line 56) are in a state of being out of communication with the other two pipe lines (water feeding pipe line 62 and water supply pipe line 56) in the space portion 59.

On the other hand, in a case in which the valve member 104 is in the spaced state, the two flow passages (flow passage 106 and flow passage 108) communicate with each other, so that all of the four pipe lines (air feeding pipe line 60, water feeding pipe line 62, air supply pipe line 54, and water supply pipe line 56) are in a state of being in communication with each other in the space portion 59. The valve member 104 of the present example is an example of a valve member according to the embodiment of the present invention. The flow passage 106 of the present example is an example of a first flow passage according to the embodiment of the present invention, and the flow passage 108 of the present example is an example of a second flow passage according to the embodiment of the present invention. It should be noted that the washing adapter 100 comprises a cap 110 to be mounted in an opening portion of the cylinder 58.

The valve member 104 is made of, for example, flexible rubber. The valve member 104 is formed in a substantially umbrella shape having an opening portion through which the shaft part 102 penetrates, as an example. In the valve member 104, in FIG. 4, a fixing part 104A having a small diameter on a lower side thereof is fixed around the shaft part 102, and a sealing part 104B having a large diameter on an upper side thereof is elastically in contact with an interior wall part 58A of the cylinder 58. That is, the valve member 104 is formed by an elastic valve.

With the valve member 104, in a case in which the pressure in the flow passage 108 is higher than the pressure in the flow passage 106 due to a fluid 204 (see FIG. 5), which will be described below, the pressure in the flow passage 108 acts on the valve member 104 as a force for pressing the sealing part 104B of the valve member 104 against the interior wall part 58A of the cylinder 58. As a result, the valve member 104 is in the contact state of being in contact with the interior wall part 58A of the cylinder 58. On the other hand, in a case in which the pressure in the flow passage 108 is lower than the pressure in the flow passage 106 due to the fluid 204 (see FIG. 5), the pressure in the flow passage 106 acts on the valve member 104 as a force for spacing the sealing part 104B of the valve member 104 apart from the interior wall part 58A of the cylinder 58. As a result, the valve member 104 is in the spaced state of being spaced apart from the interior wall part 58A of the cylinder 58, and the interior wall part 58A of the cylinder 58 that is in contact with the valve member 104 (sealing part 104B) in this case can be washed with the fluid 204 (see FIG. 5). That is, the valve member 104 of the present example is formed by a check valve that is closed in a case in which the pressure in the flow passage 108 is higher than the pressure in the flow passage 106 and that is opened in a case in which the pressure in the flow passage 106 is higher than the pressure in the flow passage 108. In other words, the valve member 104 of the present example has a function of blocking the flow of the fluid 204 from the flow passage 108 toward the flow passage 106 and allowing the flow of the fluid 204 from the flow passage 106 toward the flow passage 108.

It should be noted that, in the present example, the valve member 104 having the configuration in which the sealing part 104B is disposed above the fixing part 104A (toward the flow passage 108 side) in FIG. 4 has been described, but a valve member having a configuration in which the sealing part 104B is disposed below the fixing part 104A (toward the flow passage 106 side) may be adopted. In this case, in a case in which the pressure in the flow passage 108 is higher, the valve member 104 is in the spaced state (valve is opened), and in a case in which the pressure in the flow passage 106 is higher, the valve member 104 is in the contact state (valve is closed).

Next, the clogging determination device 200 according to the embodiment will be described with reference to FIG. 5.

Figure 5:
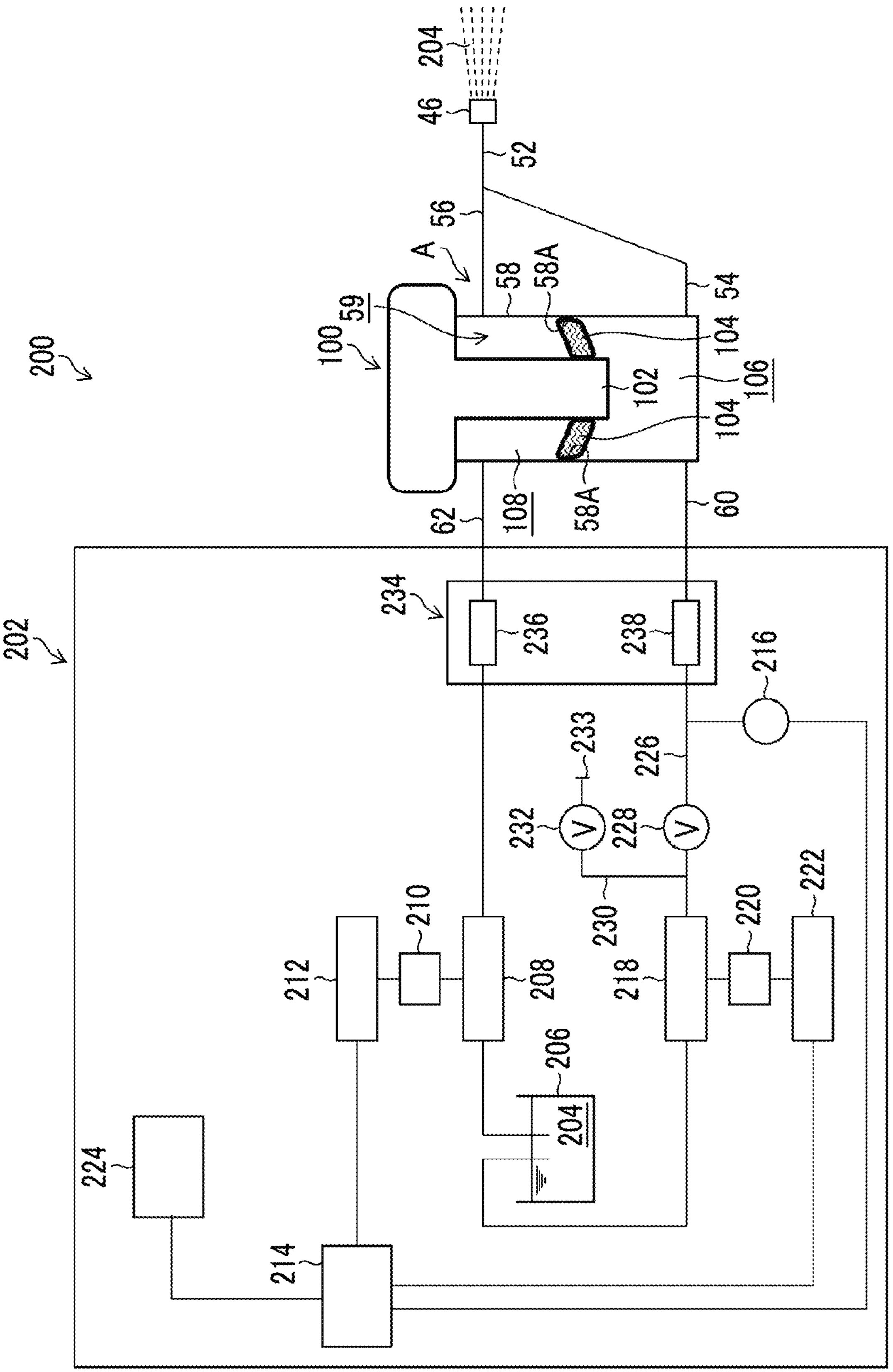
FIG. 5 is a functional block diagram of a clogging determination unit according to the embodiment.

FIG. 5 is a functional block diagram showing an example of a clogging determination unit 202 that determines the clogged state of the branch pipe line A, in the clogging determination device 200. The clogging determination unit 202 of the present example functions as a switching unit according to the embodiment of the present invention. It should be noted that, here, although the detailed overall configuration of the clogging determination device 200 is not described, the clogging determination device 200 comprises a box-shaped device body, and an accommodation tank that accommodates the endoscope 10 after the surgery is provided on an upper part of the device body.

As shown in FIG. 5, the clogging determination unit 202 comprises a tank 206 in which the fluid 204 such as a washing solution, a disinfectant solution, or alcohol is stored, a liquid supply pump 208 that supplies (that is, feeds) the fluid 204 in the tank 206 into the water feeding pipe line 62, an electric motor 210 that is a driving source of the liquid supply pump 208, a power supply 212 of the electric motor 210, a controller 214 that switches a voltage to be applied to the electric motor 210 by controlling the power supply 212 in response to an input signal, and a pressure sensor 216 that detects a back pressure of the fluid 204 in the air feeding pipe line 60.

The clogging determination unit 202 comprises a liquid supply pump 218 that supplies the fluid 204 in the tank 206 into the air feeding pipe line 60, an electric motor 220 that is a driving source of the liquid supply pump 218, and a power supply 222 of the electric motor 220. The controller 214 can switch the voltage to be applied to the electric motor 220 by controlling the power supply 222 in response to the input signal. It should be noted that the electric motors 210 and 220 are not particularly limited, and various motors such as a direct-current (DC) motor or an alternating-current (AC) motor can be adopted.

As the controller 214, a computer can be used, and the controller 214 comprises a central processing unit (CPU) (not shown), a memory such as a read only memory (ROM) (not shown) and a random access memory (RAM) (not shown), and the like. The controller 214 executes a program stored in the memory to realize various functions of the clogging determination unit 202. Various data required for the control and the like are stored in the ROM. The RAM is used as a work area in a case in which the controller 214 executes various types of processing. Further, a display unit 224 is connected to the controller 214. The display unit 224 displays, for example, the back pressure of the fluid 204 detected by the pressure sensor 216, a mark indicating whether the clogging of the branch pipe line A has occurred, or the like. It should be noted that, as the display unit 224, for example, a liquid crystal display (LCD) or an organic EL display (organic light emitting diode) can be adopted.

Hereinafter, an example of a function of the clogging determination unit 202 realized by the controller 214 will be described. It should be noted that the clogging determination unit 202 of the present example has a clogging determination function of determining the clogged state of the branch pipe line A, and also has a washing function of washing the branch pipe line A. First, the washing function will be described.

That is, the controller 214 has a washing function of realizing a branch pipe line washing mode and a cylinder interior wall washing mode within a predetermined washing time of the branch pipe line A. The washing function is mainly realized by controlling the voltages applied to the two electric motors 210 and 220.

Specifically, in the branch pipe line washing mode, the controller 214 sets the voltage to be applied to the electric motor 210 to a low voltage (for example, 12 V or 24 V) by controlling the power supply 212, rotates the electric motor 210 at a low speed to generate the fluid 204 having a low voltage, and feeds the fluid 204 having a low voltage into the water feeding pipe line 62. In this case, the electric motor 220 is in a stop state. In the branch pipe line washing mode, a solenoid valve 228 provided in a pipe line 226 between the pressure sensor 216 and the liquid supply pump 218 is opened, and a solenoid valve 232 of a liquid drain pipe line 230 provided between the solenoid valve 228 and the liquid supply pump 218 is also opened. As a result, the fluid 204 used for washing the branch pipe line A can be drained from a drain port 233 of the liquid drain pipe line 230. It should be noted that the opening and closing of the solenoid valves 228 and 232 are also executed by the controller 214.

On the other hand, in the cylinder interior wall washing mode, the controller 214 sets the voltage to be applied to the electric motor 220 to a high voltage (for example, 36 V or 48 V) by controlling the power supply 222, rotates the electric motor 220 at a high speed to generate the fluid 204 having a high voltage, and feeds the fluid 204 having a high voltage into the air feeding pipe line 60. In this case, the electric motor 210 may rotate at a low speed or may be in the stop state. In addition, in the cylinder interior wall washing mode, the solenoid valve 228 is in an opened state, and the solenoid valve 232 is in a closed state. As a result, the fluid 204 having a high voltage can be fed from the liquid supply pump 218 to the air feeding pipe line 60.

It should be noted that, as will be described in detail below, in the branch pipe line washing mode, the branch pipe line A (excluding the interior wall part 58A of the cylinder 58 that is in contact with the valve member 104 of the washing adapter 100) can be washed, and in the cylinder interior wall washing mode, the interior wall part 58A of the cylinder 58 is can be washed. The cylinder interior wall washing mode is realized at least once at a predetermined timing within the washing time of the branch pipe line A, that is, during the operation of the clogging determination unit 202. The predetermined timing can be optionally set within the washing time of the branch pipe line A. In the present example, the description will be made on the assumption that the cylinder interior wall washing mode is realized once in the latter half of the washing time.

The controller 214 has the clogging determination function for realizing a clogging determination mode. The clogging determination mode is realized in a clogged state examination step of the branch pipe line A set in a previous step of the washing step of the branch pipe line A. The clogging determination function is realized by controlling the voltage applied to the electric motor 210.

Specifically, in the clogging determination mode, the controller 214 sets the voltage to be applied to the electric motor 210 to a low voltage (for example, 12 V or 24 V) by controlling the power supply 212, rotates the electric motor 210 at a low speed to generate the fluid 204 having a low voltage, and feeds the fluid 204 having a low voltage into the water feeding pipe line 62. In this case, the electric motor 220 is in a stop state. It should be noted that the clogging determination mode is a mode in which only the clogged state of the branch pipe line A is examined, and is set in a shorter time than the washing time of the branch pipe line A. It is preferable that the clogging determination mode is also executed after the washing of the branch pipe line A. As a result, the clogged state of the branch pipe line A can be reconfirmed.

The memory of the controller 214 stores information indicating a threshold value indicating that the branch pipe line A is open, that is, a clogging determination threshold value (hereinafter, referred to as a normal back pressure range). In a case in which the back pressure detected by the pressure sensor 216 is within the normal back pressure range, the controller 214 determines that the branch pipe line A is open (no clogging has occurred in the branch pipe line A), and displays the determination result on the display unit 224. Thereafter, in a case in which the clogging determination mode ends, the controller 214 executes the branch pipe line washing mode and the cylinder interior wall washing mode. The description will be made later. In a case in which the back pressure detected by the pressure sensor 216 exceeds the normal back pressure range or is less than the normal back pressure range, the controller 214 determines that the branch pipe line A is clogged, and displays the determination result on the display unit 224. It should be noted that the pressure of the fluid 204 (rotation speed of electric motor 210) in the clogging determination mode, that is, the flow rate of the fluid 204 to be fed from the liquid supply pump 208 per unit time is set to a flow rate at which a surplus is generated, as will be described below. As a result, the back pressure can be detected by the pressure sensor 216.

Subsequently, the clogging determination unit 202 shown in FIG. 5 will be described. The clogging determination unit 202 includes a connection port 234. The connection port 234 includes two ports 236 and 238, the water feeding pipe line 62 is connected to the port 236, and the air feeding pipe line 60 is connected to the port 238.

The port 236 is connected to the liquid supply pump 208 and functions as a port for supplying the fluid 204 into the water feeding pipe line 62. The port 238 is connected to the pressure sensor 216, and functions as a port for detecting the back pressure of the fluid 204 in the air feeding pipe line 60 via the pressure sensor 216. Further, the port 238 is connected to the liquid supply pump 218 and also functions as a port for supplying the fluid 204 into the air feeding pipe line 60.

Next, the actions of the clogging determination device 200, particularly the actions of the clogging determination unit 202 will be described.

First, a clogged state examination of the branch pipe line A, which is performed before the washing of the branch pipe line A, will be described. In the clogged state examination of the present example, the air/water supply button 28 shown in FIG. 1 is removed from the cylinder 58, and the washing adapter 100 shown in FIG. 4 is attached to the cylinder 58. In this state, since the valve member 104 is in the contact state of being in contact with the interior wall of the cylinder 58, the space portion 59 of the cylinder 58 is separated into two flow passages (flow passage 106 and flow passage 108) interposing the valve member 104. Then, after accommodating the endoscope 10 in which the washing adapter 100 is mounted in the accommodation tank of the clogging determination device 200 (see FIG. 5), the water feeding pipe line 62 is connected to the port 236, and the air feeding pipe line 60 is connected to the port 238. As a result, the preparation for the clogged state examination ends. It should be noted that, in this case, both the solenoid valves 228 and 232 shown in FIG. 5 are opened. This is for removing the fluid (air and liquid) remaining in the branch pipe line A from the branch pipe line A before the back pressure is detected by the pressure sensor 216.

Next, the clogging determination mode is executed. The clogging determination mode is executed, for example, by operating an examination button provided in the device body of the clogging determination device 200. In a case in which the examination button is operated, a signal indicating the start of the examination is input to the controller 214. In this case, the controller 214 executes a setting step S10 (see FIG.

6), which will be described below, to set the voltage to be applied to the electric motor 210 to a low voltage (for example, 12 V or 24 V). By this setting step S10, the fluid 204 having a low voltage and generated by the electric motor 210 is fed to the water feeding pipe line 62.

Figure 6:
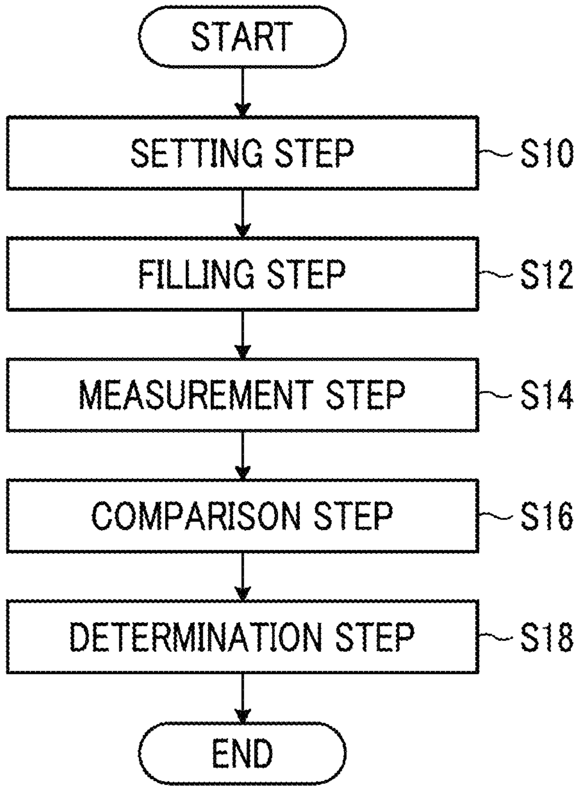
FIG. 6 is a flowchart showing an example of a clogging determination method according to the embodiment.

FIG. 6 is a flowchart showing an example of the clogging determination method according to the embodiment. As shown in FIG. 6, the clogging determination method of the present example includes the setting step S10, a filling step S12, a measurement step S14, a comparison step S16, and a determination step S18. Hereinafter, a procedure of the clogged state determination will be described with reference to the flowchart shown in FIG. 6.

In the setting step S10, in a case in which the valve member 104 disposed in the space portion 59 is brought into the contact state, at least one of the four pipe lines (air supply pipe line 54, water supply pipe line 56, air feeding pipe line 60, and water feeding pipe line 62) is in a state of being out of communication with the other pipe lines in the space portion 59.

Specifically, in the setting step S10 of the present example, as described above, the controller 214 sets the voltage to be applied to the electric motor 210 to a low voltage (for example, 12 V or 24 V), to feed the fluid 204 having a low voltage to the water feeding pipe line 62. As a result, the contact state in which the valve member 104 is in contact with the interior wall of the cylinder 58 is maintained, and two pipe lines (air supply pipe line 54 and air feeding pipe line 60) of the four pipe lines (air supply pipe line 54, water supply pipe line 56, air feeding pipe line 60, and water feeding pipe line 62) are in a state of being out of communication with the other pipe lines (water supply pipe line 56 and water feeding pipe line 62) in the space portion 59. As a result, a first pipe line route from the water feeding pipe line 62 to the air feeding pipe line 60 via the water supply pipe line 56 and the air supply pipe line 54 is set.

It should be noted that, in the setting step S10, by switching the valve member 104 to be in the spaced state of being spaced apart from the interior wall of the cylinder 58, all of the four pipe lines (air supply pipe line 54, water supply pipe line 56, air feeding pipe line 60, and water feeding pipe line 62) can also communicate with each other in the space portion 59. As a result, a second pipe line route from the air feeding pipe line 60 to the water feeding pipe line 62 (or water supply pipe line 56) via the space portion 59 is set. By selecting the second pipe line route, the interior wall of the cylinder 58 can be washed with the fluid 204.

Figure 7:
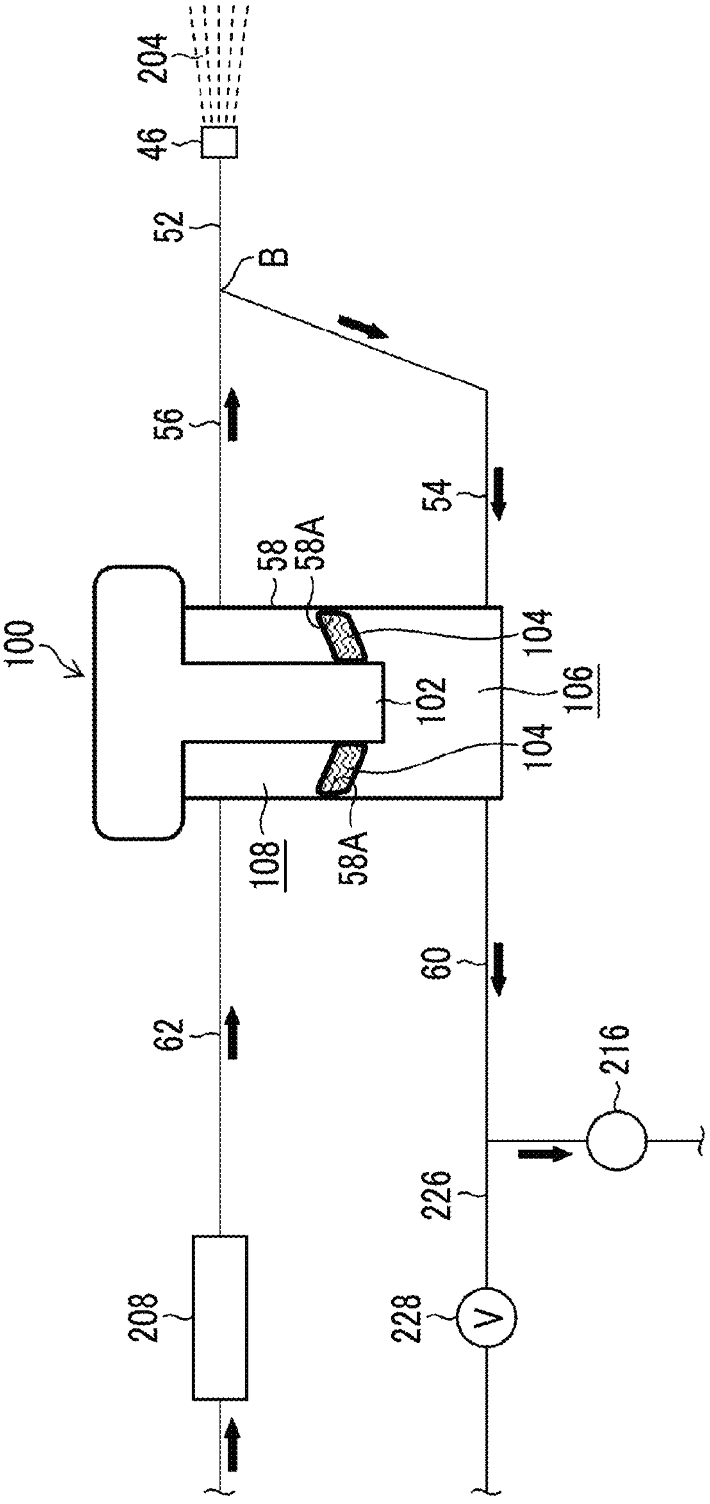
FIG. 7 is a schematic view of a branch pipe line in a case in which the branch pipe line is open.

Hereinafter, some specific examples of the clogged state examination of the branch pipe line A will be described. FIG. 7 schematically shows a state of the branch pipe line A in a case in which the branch pipe line A is open, and FIG. 8 shows a graph showing a relationship between an examination elapsed time (T) and a back pressure (P) detected by the pressure sensor 216.

As shown in FIG. 7, in a case in which the liquid supply pump 208 is driven (the rotation of the electric motor 210 is started), the fluid 204 is jetted via the air/water supply nozzle 46 from the water feeding pipe line 62 through the flow passage 108 of the cylinder 58, the water supply pipe line 56, and the air/water supply pipe line 52. The surplus of the fluid 204 is returned to the clogging determination unit 202 (see FIG. 5) from the water supply pipe line 56 through the air supply pipe line 54, the flow passage 106 of the cylinder 58, and the air feeding pipe line 60, and is drained from the drain port 233 of the liquid drain pipe line 230. As a result, the fluid (air and liquid) remaining in the branch pipe line A is drained together with the fluid 204, and the branch pipe line A is filled with the fluid 204. As a result, the filling step S12 of the flowchart shown in FIG. 6 is executed. Thereafter, the solenoid valve 228 (see FIG. 5) is switched from the opened state to the closed state to stop the drainage, and the change in the back pressure (P) after the stop is detected by the pressure sensor 216. As a result, the measurement step S14 of the flowchart shown in FIG. 6 is executed.

Figure 8:
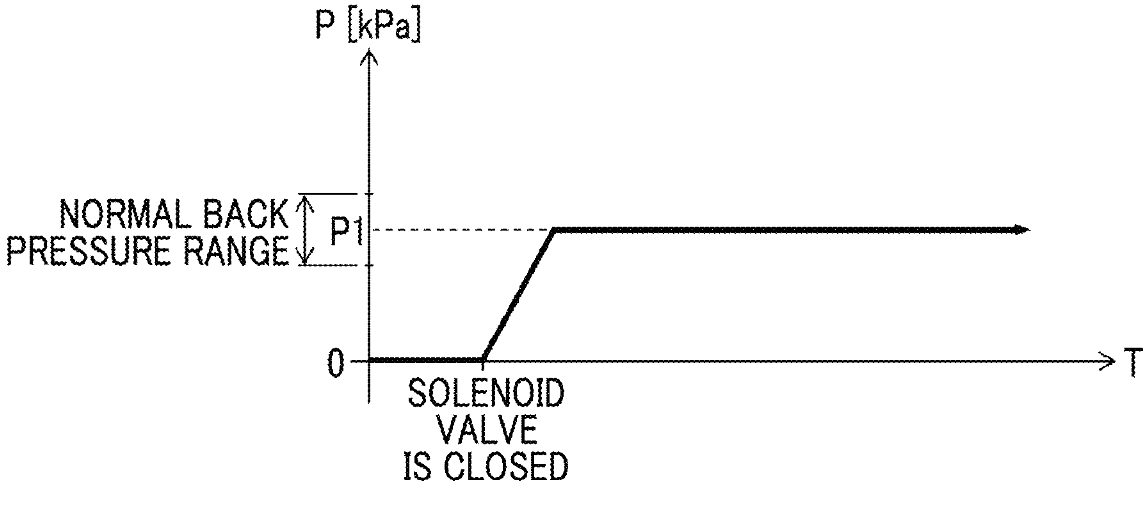
FIG. 8 is a graph showing a relationship between an examination elapsed time and an output value of a pressure sensor.

As shown in FIG. 8, in a case in which the solenoid valve 228 is switched to the closed state (solenoid valve is closed), the back pressure (P) detected by the pressure sensor 216 increases with the lapse of time, and then the back pressure reaches a certain value (P1). In the comparison step S16 of the flowchart shown in FIG. 6, the back pressure (P1) that has reached a certain value and the normal back pressure range are compared with each other. In the determination step S18 of the flowchart shown in FIG. 6, since the back pressure (P1) is within the normal back pressure range, the controller 214 shown in FIG. 5 determines that the branch pipe line A is open (that is, determines that no clogging has occurred in the branch pipe line A), and displays the determination result on the display unit 224. It should be noted that, in the clogging determination mode, the fluid 204 may be leaked from the opening portion of the cylinder 58 to wash an opening edge portion of the cylinder 58 with the fluid 204. Even in this case, the clogged state can be detected without any problem by changing the normal back pressure range, which is the threshold value, based on the leakage amount of the fluid 204.

Figure 9:
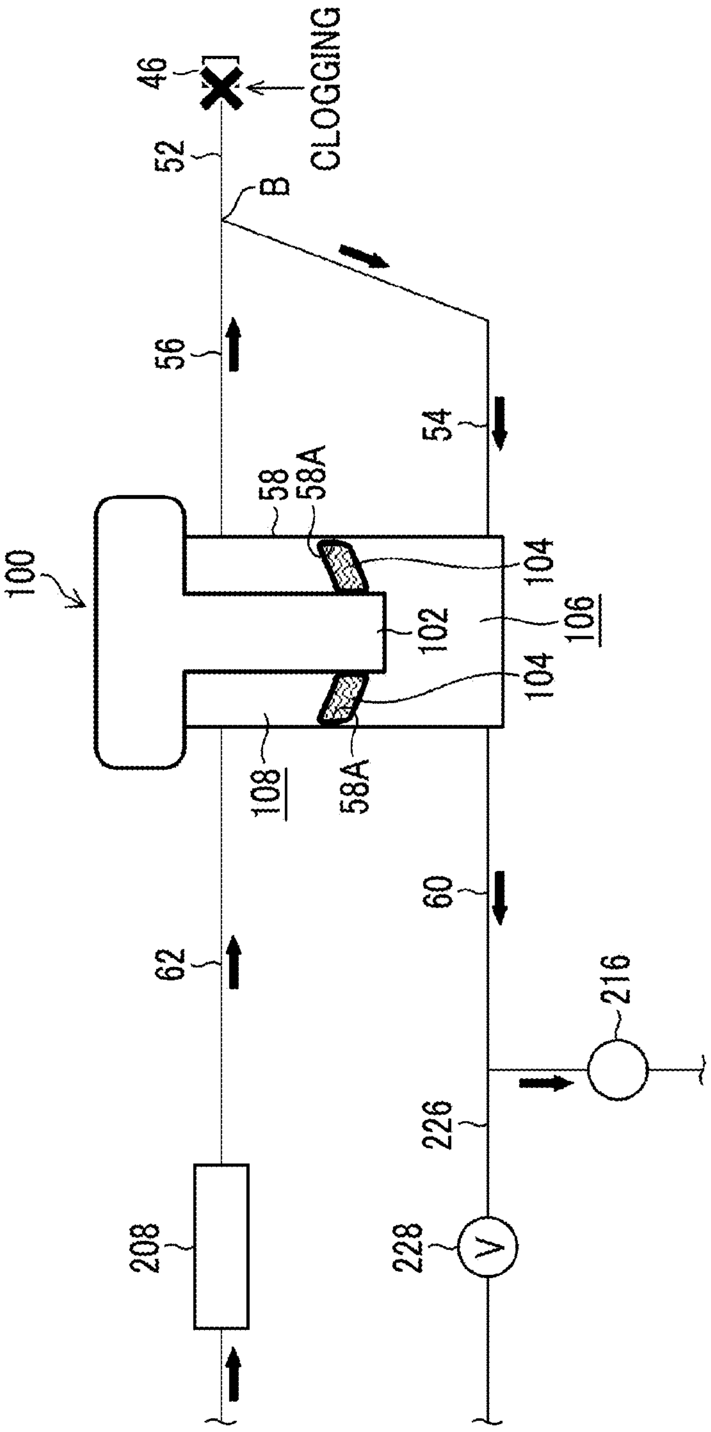
FIG. 9 is a schematic view of the branch pipe line in a case in which the clogging has occurred in the branch pipe line.
Figure 10:
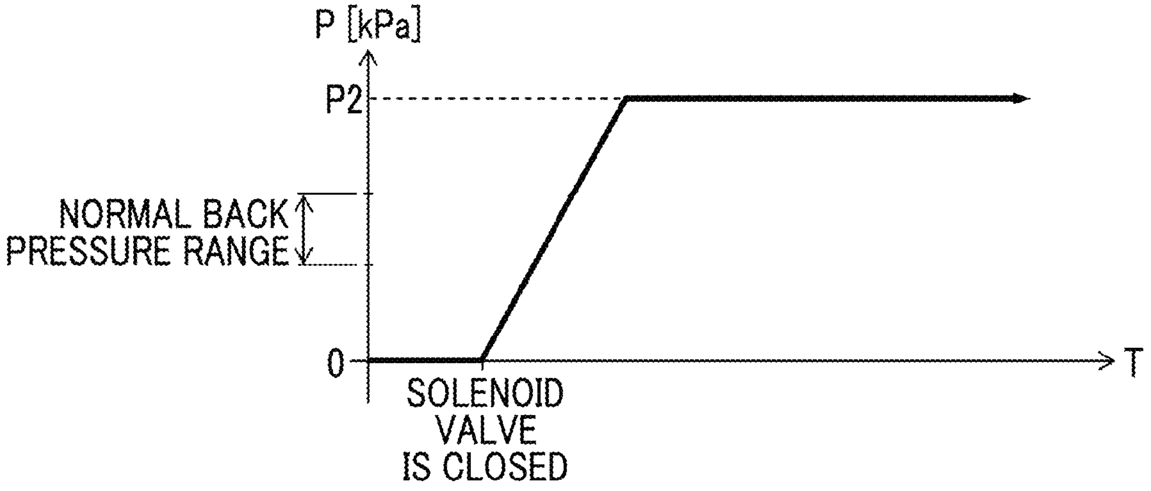
FIG. 10 is a graph showing a relationship between the examination elapsed time and the output value of the pressure sensor.

FIG. 9 schematically shows a state of the branch pipe line A in a case in which the clogging has occurred at a position of the air/water supply pipe line 52 in the branch pipe line A, and FIG. 10 shows a graph showing a relationship between the examination elapsed time (T) and the back pressure (P) detected by the pressure sensor 216.

In a case in which the clogging has occurred at the position of the air/water supply pipe line 52 in the branch pipe line A as shown in FIG. 9, as shown in FIG. 10, in a case in which the solenoid valve 228 (see FIG. 5) is in the closed state (solenoid valve is closed), the back pressure detected by the pressure sensor 216 increases with the lapse of time, and then the back pressure reaches a certain value (P2). The example of FIG. 10 shows that the back pressure (P2) that has reached a certain value exceeds the normal back pressure range, and as a result, the controller 214 shown in FIG. 5 determines that the clogging has occurred in the branch pipe line A and displays the determination result on the display unit 224.

Figure 11:
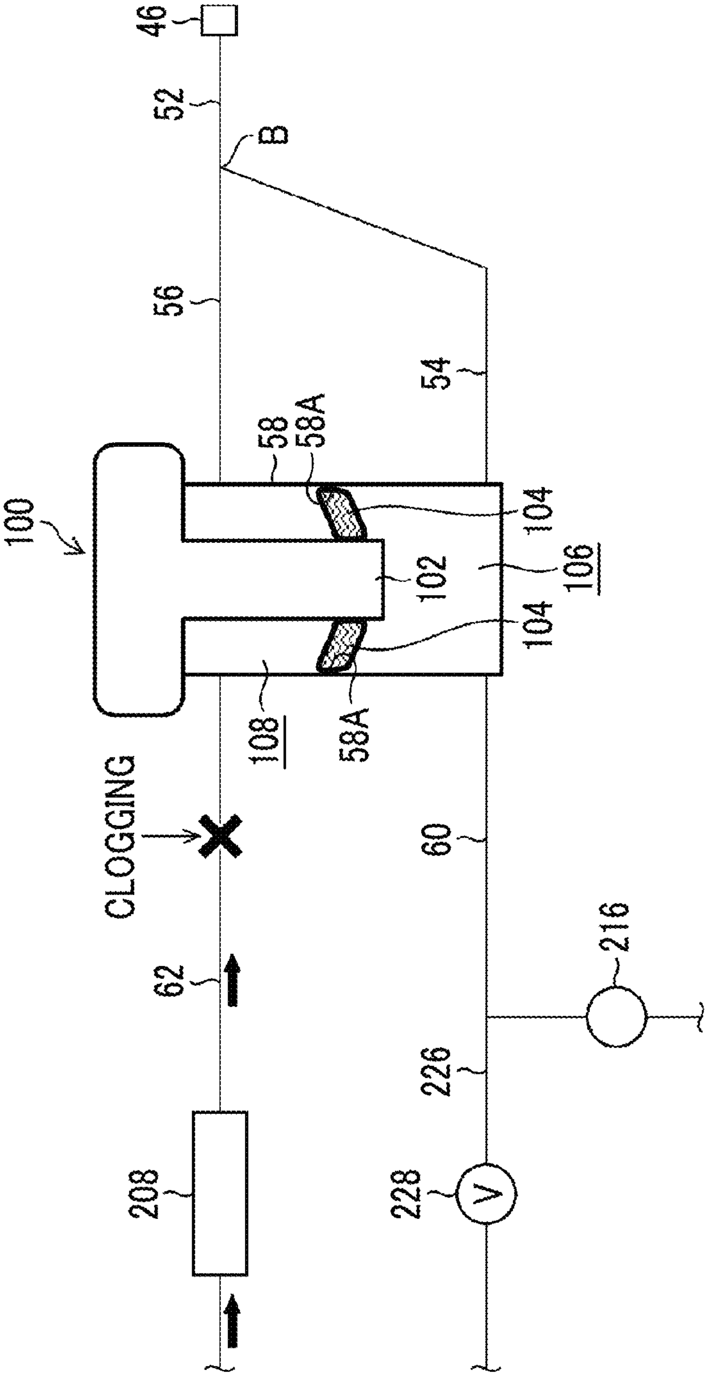
FIG. 11 is a schematic view of the branch pipe line in a case in which the clogging has occurred in the branch pipe line.
Figure 12:
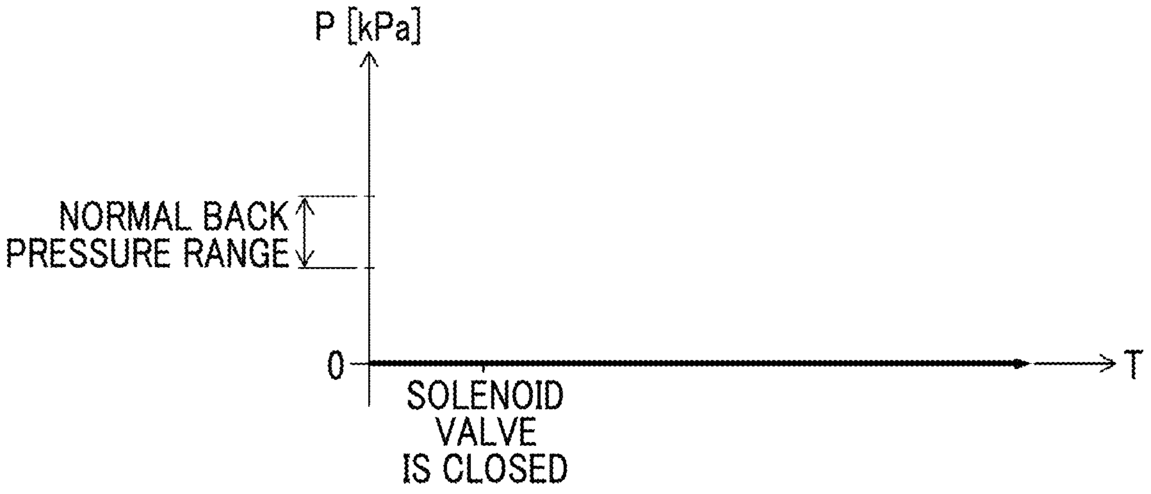
FIG. 12 is a graph showing a relationship between the examination elapsed time and the output value of the pressure sensor.

FIG. 11 schematically shows a state of the branch pipe line A in a case in which the clogging has occurred at a position of the water feeding pipe line 62 in the branch pipe line A, and FIG. 12 shows a graph showing a relationship between the examination elapsed time (T) and the back pressure (P) detected by the pressure sensor 216.

In a case in which the clogging has occurred at the position of the water feeding pipe line 62 in the branch pipe line A as shown in FIG. 11, as shown in FIG. 12, even after the solenoid valve 228 (see FIG. 5) is in the closed state (solenoid valve is closed), the back pressure detected by the pressure sensor 216 remains in a state of 0 (zero). The example of FIG. 12 shows that the back pressure (zero) is less than the normal back pressure range, and as a result, the controller 214 shown in FIG. 5 determines that the clogging has occurred in the branch pipe line A and displays the determination result on the display unit 224.

Here, the branch pipe lines A shown in FIGS. 9 and 11 are both in a state in which the clogging has occurred, but patterns of the clogging occurring in the branch pipe line A include a first pattern in which the clogging has occurred in the pipe lines (water feeding pipe line 62, water supply pipe line 56, air supply pipe line 54, and air feeding pipe line 60) on the base end side with respect to a branch part (a part in which the air supply pipe line 54 and the water supply pipe line 56 branch from the air/water supply pipe line 52, that is, a part in which the air supply pipe line 54 and the water supply pipe line 56 are combined, hereinafter, referred to as a branch part B) of the branch pipe line A as shown in FIG. 11, and a second pattern in which the clogging has occurred in the pipe line (air/water supply pipe line 52) on the distal end side with respect to the branch part B as shown in FIG. 9. The controller 214 determines whether the pattern of the clogging is the first pattern or the second pattern based on the back pressure detected by the pressure sensor 216, and displays the determined pattern on the display unit 224.

Specifically, in a case in which the back pressure is the back pressure (P2) shown in the graph of FIG. 10, the back pressure (P) exceeds the normal back pressure range, and thus it is determined that the pattern is the second pattern in which the clogging has occurred in the air/water supply pipe line 52 (see FIG. 9) on the distal end side with respect to the branch part B, and the fact that the pattern is the second pattern is displayed on the display unit 224. On the other hand, in a case in which the back pressure is the back pressure (zero) shown in the graph of FIG. 12, the back pressure is less than the normal back pressure range, and thus it is determined that the pattern is the first pattern in which the clogging has occurred in at least one (in the present example, the water feeding pipe line 62) of the pipe lines (water feeding pipe line 62, water supply pipe line 56, air supply pipe line 54, and air feeding pipe line 60) on the base end side with respect to the branch part B, and the fact that the pattern is the first pattern is displayed on the display unit 224. It should be noted that the same applies to a case in which the clogging has occurred in the pipe line on the base end side other than the water feeding pipe line 62.

Therefore, with the clogging determination device 200 according to the embodiment, the configuration has been adopted in which the clogging determination unit 202 brings the valve member 104 into the contact state, and the two pipe lines (air supply pipe line 54 and air feeding pipe line 60) of the four pipe lines (air supply pipe line 54, water supply pipe line 56, air feeding pipe line 60, and water feeding pipe line 62) are in a state of being out of communication with the other pipe lines (water supply pipe line 56 and water feeding pipe line 62) in the space portion 59, so that it is possible to detect the clogging even in a case in which the clogging occurs in any pipe line in the branch pipe line A. That is, in the technology of WO2015/125347A, even in a case in which the clogging has occurred in the air/water supply pipe line 52, the clogging cannot be detected, but in the clogging determination device 200 according to the embodiment, the clogging of the air/water supply pipe line 52 can be detected. As a result, the clogging detection performance in the branch pipe line A is improved.

Next, the branch pipe line washing mode and the cylinder interior wall washing mode for washing the branch pipe line A will be described with reference to FIG. 5.

First, the branch pipe line washing mode is executed. The branch pipe line washing mode is executed, for example, by operating a pipe line washing button provided in the device body of the clogging determination device 200. In a case in which the pipe line washing button is operated, a signal indicating the start of the washing is input to the controller 214. In this case, the controller 214 sets the voltage to be applied to the electric motor 210 to a low voltage (for example, 12 V or 24 V), rotates the electric motor 210 at a low speed to generate the fluid 204 having a low voltage, and feeds the fluid 204 having a low voltage into the water feeding pipe line 62 from the port 236.

The fluid 204 is jetted via the air/water supply nozzle 46 from the water feeding pipe line 62 through the flow passage 108 of the cylinder 58, the water supply pipe line 56, and the air/water supply pipe line 52. As a result, the water feeding pipe line 62, the flow passage 108 of the cylinder 58, the water supply pipe line 56, the air/water supply pipe line 52, and the air/water supply nozzle 46 are washed with the fluid 204. Then, the surplus of the fluid 204 is returned to the clogging determination unit 202 from the water supply pipe line 56 through the air supply pipe line 54, the flow passage 106 of the cylinder 58, and the air feeding pipe line 60. In this case, since the solenoid valves 228 and 232 are in the opened state in advance, the fluid 204 returned to the clogging determination unit 202 is drained from the drain port 233 of the liquid drain pipe line 230. As a result, the air supply pipe line 54, the flow passage 106 of the cylinder 58, and the air feeding pipe line 60 are washed with the fluid 204.

Meanwhile, in a case in which the branch pipe line A is washed in the branch pipe line washing mode, as shown in FIG. 4, the valve member 104 of the washing adapter 100 is in the contact state. Therefore, a wall surface that defines the flow passage 106 and a wall surface that defines the flow passage 108 among the interior walls of the cylinder 58 are washed with the fluid 204, but the interior wall part 58A of the cylinder 58, which is in contact with the valve member 104, is not in contact with the fluid 204 and thus is in an unwashed state. Therefore, the cylinder interior wall washing mode for washing the interior wall part 58A is executed.

The cylinder interior wall washing mode is executed at least once within the washing time as described above, and is set to be executed in the latter half of the washing time in the present example. In the cylinder interior wall washing mode, the controller 214 controls the power supply 222 to set the voltage to be applied to the electric motor 220 to a high voltage (for example, 36 V or 48 V), rotates the electric motor 220 at a high speed to generate the fluid 204 having a high voltage, and feeds the fluid 204 having a high voltage into the air feeding pipe line 60. In this case, the solenoid valve 228 is in the opened state, the solenoid valve 232 is in the closed state, and the electric motor 210 is in the stop state. In this case, since the fluid 204 having a high voltage and a high flow rate is supplied into the flow passage 106 of the cylinder 58, the pressure in the flow passage 106 is higher than the pressure in the flow passage 108, so that the valve member 104 is in the spaced state in which the sealing part 104B is spaced apart from the interior wall part 58A of the cylinder 58. As a result, the pipe line route is switched from the first pipe line route to the second pipe line route, and the interior wall part 58A in the unwashed state and in contact with the valve member 104 (sealing part 104B) is washed with the fluid 204. As a result, the interior wall of the cylinder 58 including the interior wall part 58A can be reliably washed, and thus the washing performance of the interior wall of the cylinder is improved.

As described above, the clogging determination device 200 according to the embodiment adopts the configuration in which the washing adapter 100 including the valve member 104 that is switchable between the contact state and the spaced state, and the clogging determination unit 202 that switches the valve member 104 between the contact state and the spaced state are provided, so that it is possible to achieve both the improvement of the washing performance of the interior wall of the cylinder and the improvement of the pipe line clogging detection performance.

The clogging determination device 200 according to the embodiment adopts the configuration in which the valve member 104 is switched between the contact state and the spaced state by adjusting the pressure (flow rate) of the fluid 204. With this configuration, a threshold value for switching the valve member 104 between the contact state and the spaced state can be set to the voltage applied to the electric motors 210 and 220. As a result, even in the endoscope of which the pipe line resistance is different for each model, it is only necessary to set the voltage (threshold value) corresponding to the model, so that the clogged state of the pipe line can be detected without additional effort as compared with the clogging determination device (for example, see WO2015/125347A) that needs to be provided with the separator corresponding to each model.

In the cylinder interior wall washing mode, the example in which the electric motor 210 is stopped during the driving of the electric motor 220 has been described, but the present invention is not limited to this, and the cylinder interior wall washing mode may be executed in a state in which both the electric motors 210 and 220 are driven. In this case, since it is necessary to bring the valve member 104 into the spaced state, the electric motor 210 may be rotated at a lower speed than the electric motor 220 to reduce the pressure in the flow passage 108 to be lower than the pressure in the flow passage 106.

That is, in the clogging determination device 200 according to the embodiment, in the clogging determination mode and the branch pipe line washing mode, the valve member 104 can be maintained in the contact state by supplying the fluid 204 from the water feeding pipe line 62 into the space portion 59 of the cylinder 58. In the cylinder interior wall washing mode, the valve member 104 can be switched to the spaced state by supplying the fluid 204 from the air feeding pipe line 60 (including the water feeding pipe line 62) into the space portion 59 of the cylinder 58. That is, the clogging determination device 200 according to the embodiment can change the supply condition (pressure and flow rate) of the fluid 204 supplied from at least one (some pipe line) of the water feeding pipe line 62 or the air feeding pipe line 60 to the space portion 59 of the cylinder 58, to switch the valve member 104 between the contact state and the spaced state.

Hereinafter, some modification examples of the valve member constituting the washing adapter 100 will be described.

Figure 13:
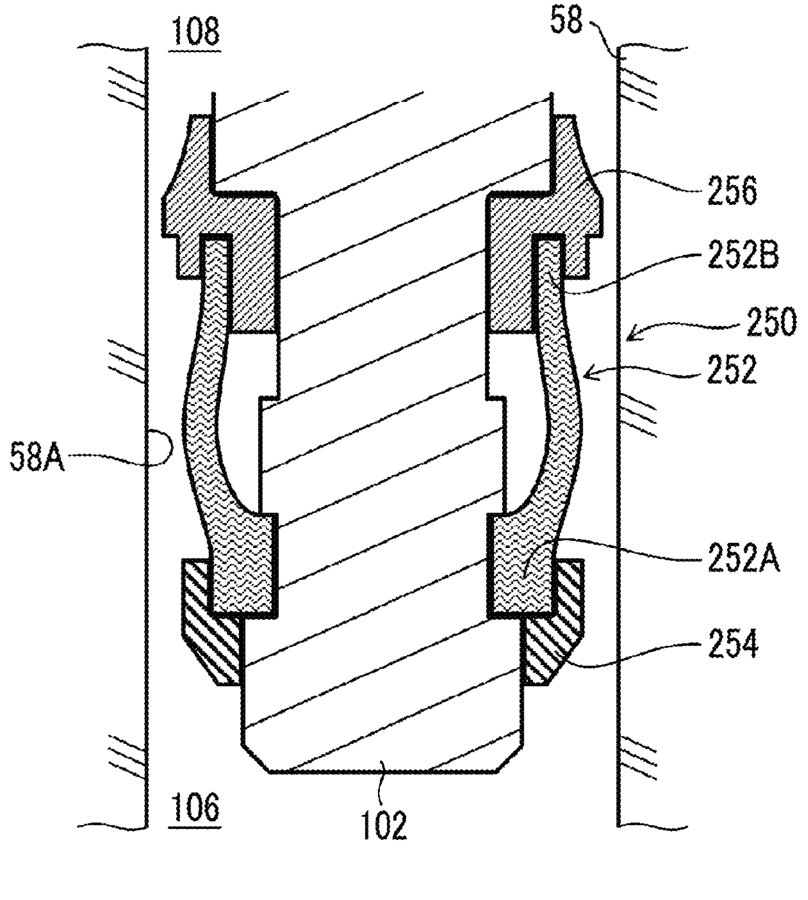
FIG. 13 is a cross-sectional view showing a first modification example of a valve member constituting the washing adapter.

FIG. 13 is a longitudinal cross-sectional view of a valve member 250 according to a first modification example. It should be noted that the same reference numerals are added to the same members as the members of the washing adapter 100 shown in FIG. 4.

As shown in FIG. 13, the valve member 250 is formed by a tubular flexible member 252 that covers an outer periphery of the shaft part 102. Among both end parts of the flexible member 252 in the axial direction of the shaft part 102, one end part of the shaft part 102 of the flexible member 252 is formed as a fixing part 252A fixed to the shaft part 102. The fixing part 252A is fixed to the outer periphery of the shaft part 102 by, for example, an annular fastener 254. An annular member 256 that is movable in the axial direction of the shaft part 102 is attached to the other end part of the flexible member 252. As a result, the other end part of the flexible member 252 is formed as a movable part 252B that is movable in the axial direction of the shaft part 102 in conjunction with the movement of the annular member 256. The flexible member 252 is made of, for example, rubber.

In a case in which the movable part 252B is located at a restriction position at which the movement of the movable part 252B in a direction away from the fixing part 252A is restricted (a position at which the flexible member 252 extends in the axial direction of the shaft part 102: a position in FIG. 13), the flexible member 252 is decreased in diameter and is in the spaced state. On the other hand, in a case in which the movable part 252B is moved in a direction toward the fixing part 252A from the restriction position, as shown in the cross-sectional view of FIG. 14, the flexible member 252 is increased in diameter to be elastically in contact with the interior wall of the cylinder 58, and is in the contact state. The valve member 250 of the present example is also an example of an elastic valve.

With the valve member 250, in a case in which, out of the pressure in the flow passage 106 and the pressure in the flow passage 108, the pressure in the flow passage 108 is higher than the pressure in the flow passage 106, the movable part 252B is moved in a direction toward the fixing part 252A via the pressure in the flow passage 108. As a result, the flexible member 252 is increased in diameter and is in the contact state (see FIG. 14). On the other hand, in a case in which the pressure in the flow passage 108 is lower than the pressure in the flow passage 106, the movable part 252B is moved from the fixing part 252A toward the restriction position via the pressure in the flow passage 106. As a result, the flexible member 252 is decreased in diameter and is in the spaced state (see FIG. 13). As a result, the interior wall part 58A of the cylinder 58 that is in contact with the flexible member 252 can be washed with the fluid 204. The valve member 250 of the present example is also an example of a check valve.

Figure 14:
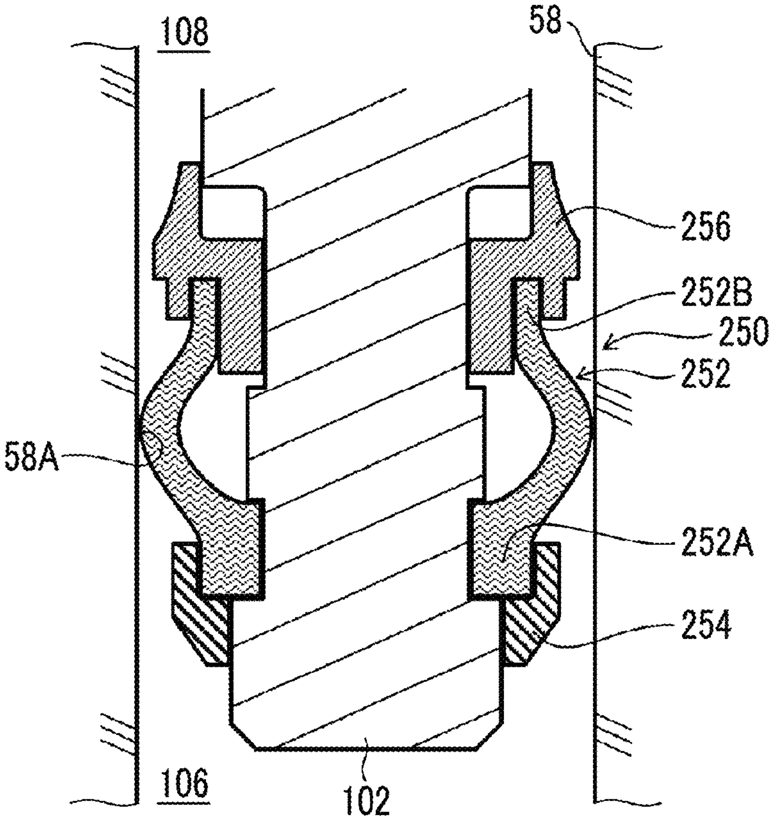
FIG. 14 is an operation explanatory diagram of the valve member shown in FIG. 13.

Since the valve member 250 of the present example adopts the configuration in which the movable part 252B is movable with respect to the shaft part 102 via the annular member 256, as shown in FIGS. 13 and 14, the movable part 252B made of rubber can be protected by the annular member 256. As a result, it is possible to extend the service life of the movable part 252B, in other words, the service life of the valve member 250.

Figure 15:
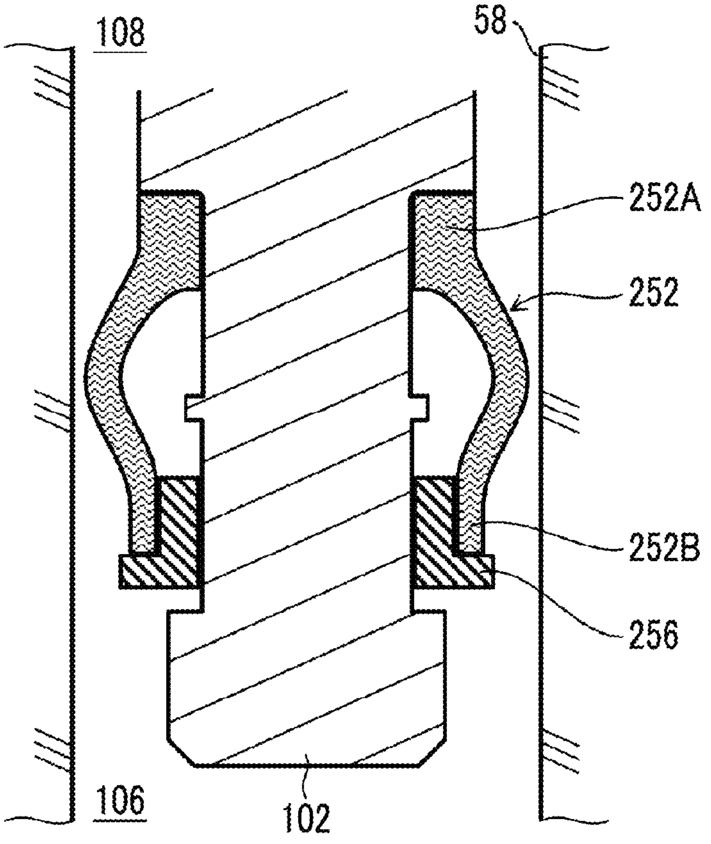
FIG. 15 is a cross-sectional view showing a modification example of the valve member shown in FIG. 13.

In the valve member 250 shown in FIGS. 13 and 14, the configuration is shown in which the lower end of the flexible member 252 is the fixing part 252A and the upper end is the movable part 252B in FIGS. 13 and 14, but the present invention is not limited to this. For example, as in the flexible member 252 shown in FIG. 15, the lower end of the flexible member 252 may be the movable part 252B, and the upper end may be the fixing part 252A. In this case, in a case in which, out of the pressure in the flow passage 106 and the pressure in the flow passage 108, the pressure in the flow passage 108 is higher than the pressure in the flow passage 106, the flexible member 252 is decreased in diameter and is in the spaced state. On the other hand, in a case in which the pressure in the flow passage 108 is lower than the pressure in the flow passage 106, the flexible member 252 is increased in diameter and is in the contact state.

Figure 16:
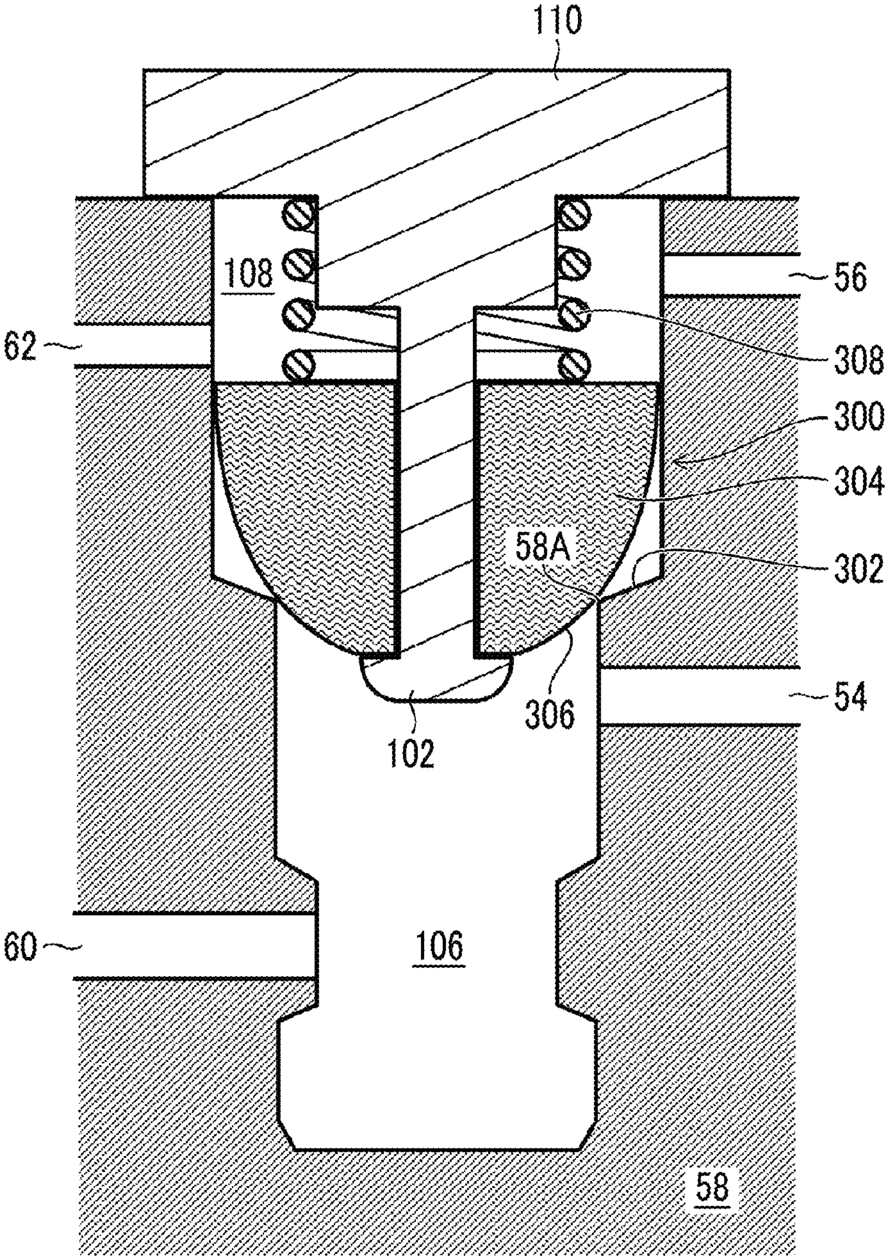
FIG. 16 is a cross-sectional view showing a second modification example of the valve member constituting the washing adapter.

FIG. 16 is a longitudinal cross-sectional view of a valve member 300 according to a second modification example. It should be noted that the same reference numerals are added to the same members as the members of the washing adapter 100 shown in FIG. 4.

As shown in FIG. 16, the valve member 300 includes a valve body 304 that has a hemispherical shape and is configured to abut on a stepped part 302 provided on the interior wall of the cylinder 58, and a spring 308 that biases a spherical surface 306 of a lower side of the valve body 304 in a direction of abutting on the stepped part 302. The spring 308 is disposed to surround the shaft part 102 and is disposed between the valve body 304 and the cap 110. The stepped part 302 of the present example is an example of an abutting target part according to the embodiment of the present invention, the valve body 304 of the present example is an example of an abutting member according to the embodiment of the present invention, and the spring 308 of the present example is an example of a biasing member according to the embodiment of the present invention.

With the valve member 300, in a case in which, out of the pressure in the flow passage 106 and the pressure in the flow passage 108, the pressure in the flow passage 108 is higher than the pressure in the flow passage 106, the valve body 304 abuts on the stepped part 302 via the biasing force of the spring 308 and is in the contact state. On the other hand, in a case in which the pressure in the flow passage 108 is lower than the pressure in the flow passage 106, the valve body 304 is spaced apart from the stepped part 302 toward the flow passage 108 side against the biasing force of the spring 308 and is in the spaced state. As a result, the stepped part (interior wall part) 302 of the cylinder 58 that is in contact with the valve body 304 can be washed with the fluid 204. The valve member 300 of the present example is also an example of a check valve.

It should be noted that, in the present example, the configuration has been described in which the stepped part 302 is shown as the abutting target part according to the embodiment of the present invention and the valve body 304 is shown as the abutting member according to the embodiment of the present invention, but the present invention is not limited to this configuration. That is, the abutting target part and the abutting member may have any shape as long as the abutting target part and the abutting member are in the contact state in a case in which the abutting member abuts on the abutting target part, and for example, a configuration in which an annular flange (abutting target part) is provided on the interior wall surface of the cylinder 58 and a disk (abutting member) abuts on the flange such that the flange and the disk are in the contact state can also be applied. In addition, in the present example, the configuration has been described in which the spring 308 is shown as the biasing member according to the embodiment of the present invention, but the present invention is not limited to this configuration. That is, the biasing member need only have a function of biasing the abutting member in a direction of abutting on the abutting target part, and for example, a spring washer can also be applied.

Figure 17:
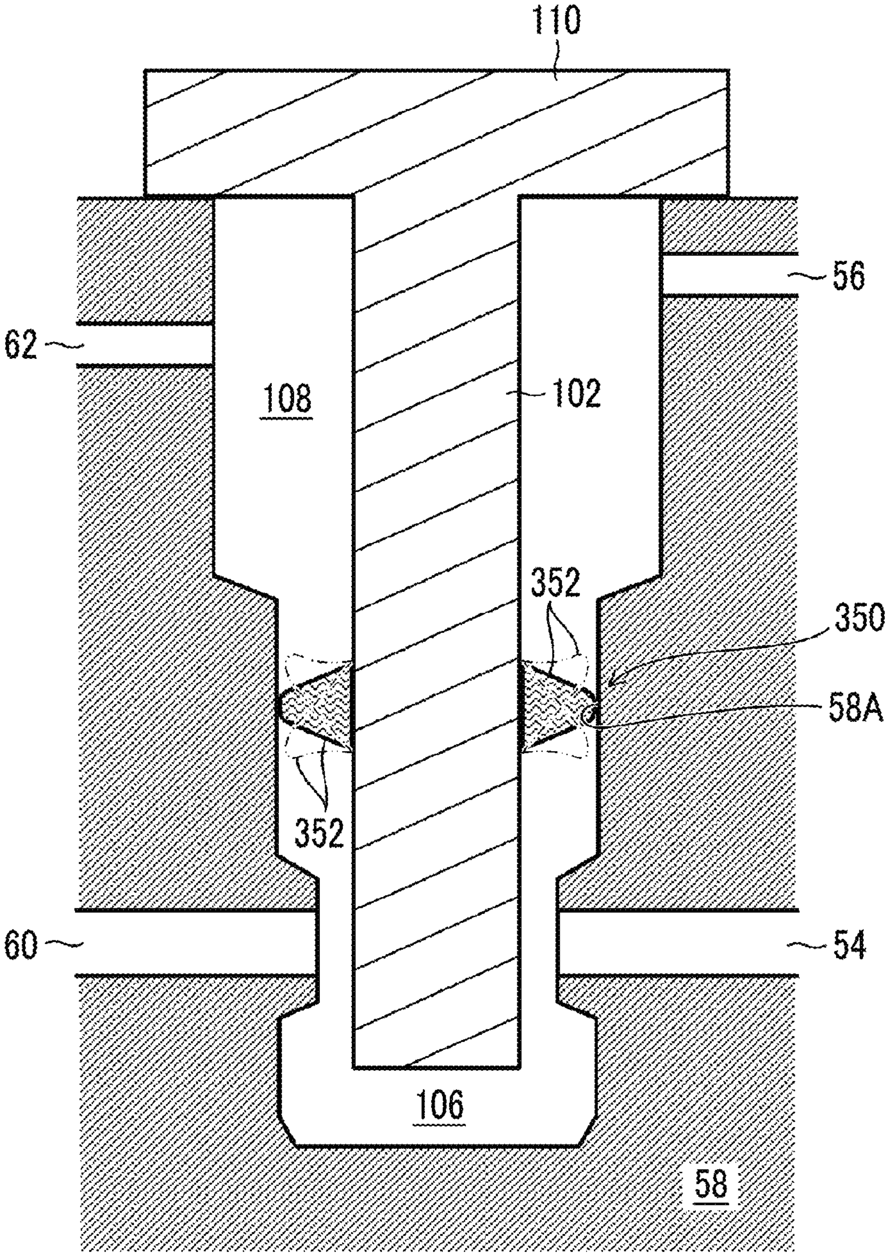
FIG. 17 is a cross-sectional view showing a third modification example of the valve member constituting the washing adapter.

FIG. 17 is a longitudinal cross-sectional view of a valve member 350 according to a third modification example. It should be noted that the same reference numerals are added to the same members as the members of the washing adapter 100 shown in FIG. 4.

As shown in FIG. 17, the valve member 350 includes a tapered part 352 in which a thickness of a cross section orthogonal to the axial direction of the shaft part 102 is smaller as a distance to the interior wall of the cylinder 58 is smaller. The valve member 350 is made of, for example, rubber.

The valve member 350 is formed by, for example, an elastic valve in which the tapered part 352 is elastically in contact with the interior wall surface of the cylinder 58 in a case in which the fluid 204 (see FIG. 5) is not present in the flow passage 106 and the flow passage 108. In a case in which the pressure difference between the inside of the flow passage 106 and the inside of the flow passage 108 is smaller than a threshold pressure difference, the valve member 350 is maintained in the contact state, and in a case in which the pressure difference is larger than the threshold pressure difference, the valve member 350 is in the spaced state.

Specifically, in a case in which the pressure in the flow passage 106 is larger than the pressure in the flow passage 108 by the threshold pressure difference (for example, 10 kPa), the tapered part 352 is elastically deformed in a direction of being spaced apart from the interior wall part 58A of the cylinder 58 and being inclined toward the flow passage 108 side due to the pressure difference. On the contrary, in a case in which the pressure in the flow passage 108 is larger than the pressure in the flow passage 106 by the threshold pressure difference, the tapered part 352 is elastically deformed in a direction of being spaced apart from the interior wall part 58A of the cylinder 58 and being inclined toward the flow passage 106 side due to the pressure difference. In any case, the interior wall part 58A of the cylinder 58 that is in contact with the tapered part 352 can be washed with the fluid 204.

It should be noted that, in the present example, the valve member 350 having the tapered part 352 has been described as an example, but the present invention is not limited to this, and the present invention can be applied to a valve member having a function of being able to switch between the contact state and the spaced state based on the threshold pressure difference. For example, a valve member having a uniform thickness of the cross section orthogonal to the axial direction of the shaft part 102 can also be applied. However, since the valve member 350 described in the present example has the tapered part 352, the valve member 350 can be switched between the contact state and the spaced state with a good response based on the threshold pressure difference.

Figure 18:
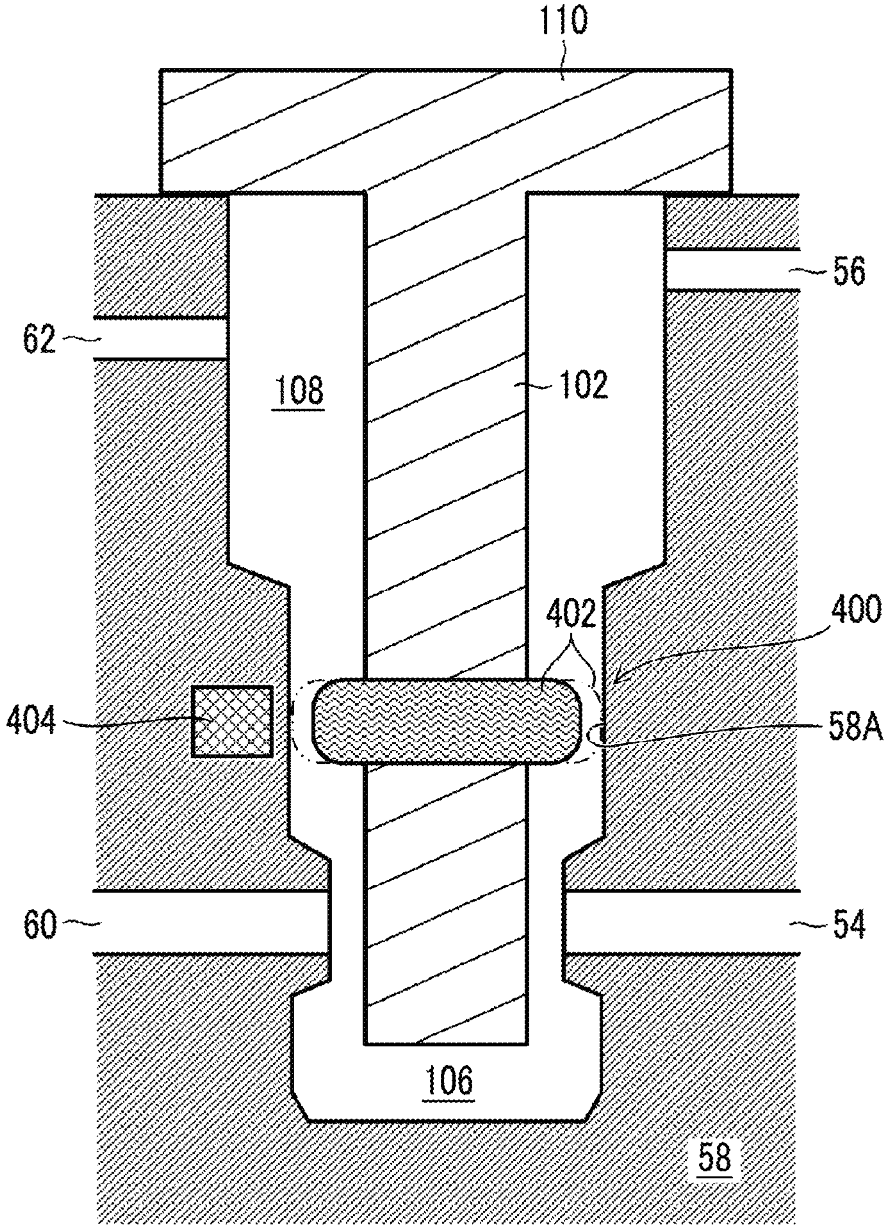
FIG. 18 is a cross-sectional view showing a fourth modification example of the valve member constituting the washing adapter.

FIG. 18 is a longitudinal cross-sectional view of a valve member 400 according to a fourth modification example. It should be noted that the same reference numerals are added to the same members as the members of the washing adapter 100 shown in FIG. 4.

As shown in FIG. 18, the valve member 400 is formed by a temperature deformable member 402 that is deformable between the contact state (two-point chain line) and the spaced state (solid line) according to a temperature change, as indicated by a solid line and a two-point chain line. Examples of the temperature deformable member 402 include a member made of plastic such as polyethylene having a large thermal expansion coefficient. The temperature deformable member 402 is deformed between the contact state and the spaced state by changing the temperature of the fluid 204 supplied into the cylinder 58, for example.

Specifically, the temperature deformable member 402 is thermally expanded to be in the contact state by setting the temperature of the fluid 204 applied to the temperature deformable member 402 to be equal to or higher than a deformable temperature (for example, 50 degrees) at which the temperature deformable member 402 is deformable, and the temperature deformable member 402 is thermally contracted to be in the spaced state by setting the temperature of the fluid 204 to be lower than the deformable temperature. As a result, the interior wall part 58A of the cylinder 58, which is in contact with the temperature deformable member 402, can be washed with the fluid 204 (see FIG. 5).

Since a sterilizing effect of the disinfectant solution in the fluid 204 varies depending on a normal temperature, the disinfectant solution is often temperature-controlled. It is preferable to thermally expand or thermally contract the temperature deformable member 402 using the temperature-controlled disinfectant solution to deform the temperature deformable member 402 between the contact state and the spaced state. The present invention is not limited to the disinfectant solution, and the temperature of another fluid (washing solution or alcohol) 204 may be controlled to deform the temperature deformable member 402 between the contact state and the spaced state.

As a unit that controls the temperature of the fluid 204, a unit that heats the fluid 204 in the tank 206 by attaching a heat transfer member (not shown) to the tank 206 shown in FIG. 5 can be shown. As another unit, a heat transfer member 404 (see FIG. 18) may be attached to an outer wall of the cylinder 58. In this case, the fluid 204 in the cylinder 58 can be heated to a desired temperature by heating the cylinder 58 via the heat transfer member 404.

It should be noted that, in the present example, the member made of plastic such as polyethylene has been described as the temperature deformable member 402, but the present invention is not limited to this, and for example, a balloon filled with air can also be applied. The temperature deformable member 402 of the present example has been described with reference to a member that is thermally expanded by heating, but the present invention is not limited to this, and a member that is thermally contracted by heating can also be applied. In a case of this member, the spaced state is obtained by heating, and the contact state is obtained by cooling.

Figure 19:
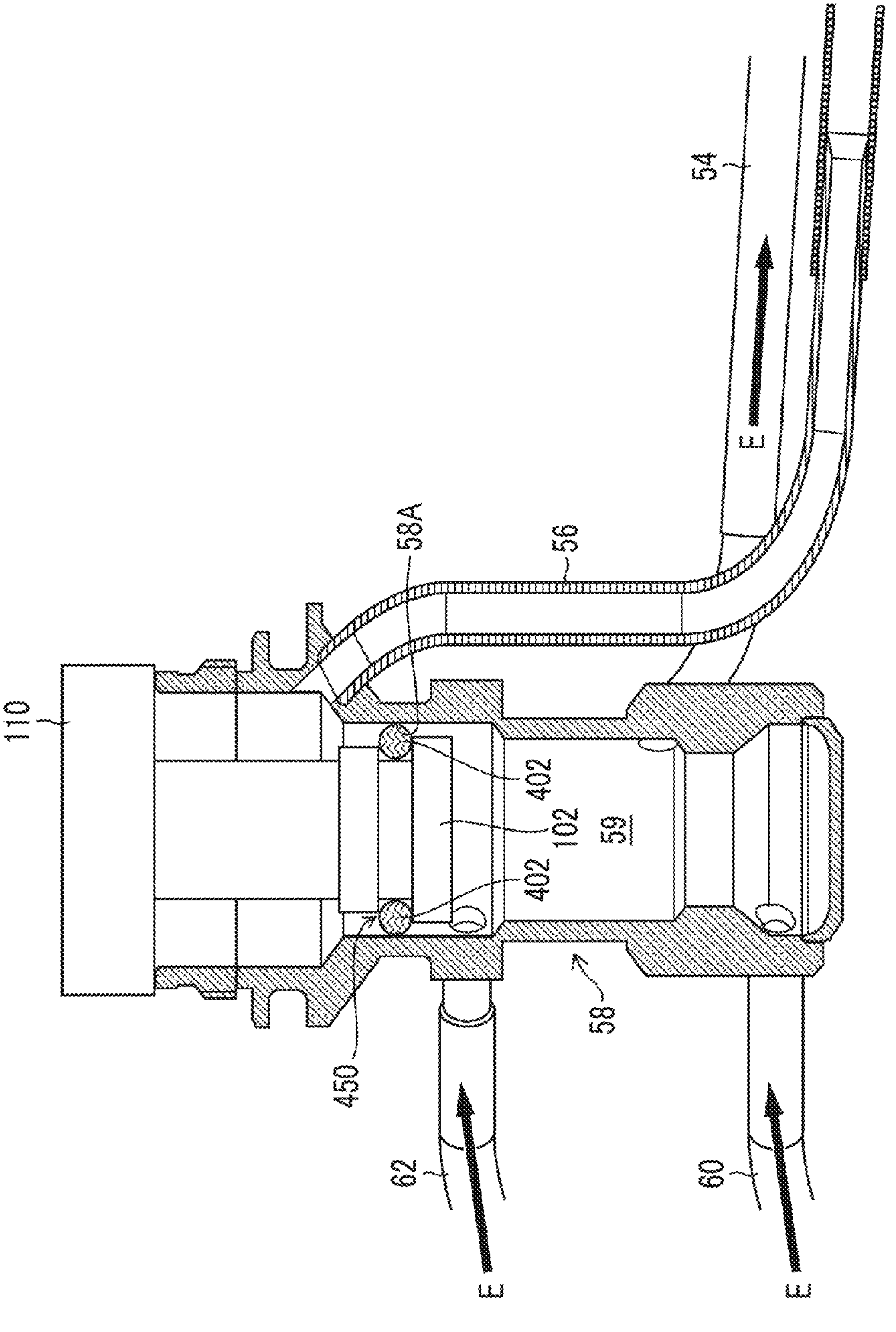
FIG. 19 is a cross-sectional view showing a fifth modification example of the valve member constituting the washing adapter.
Figure 20:
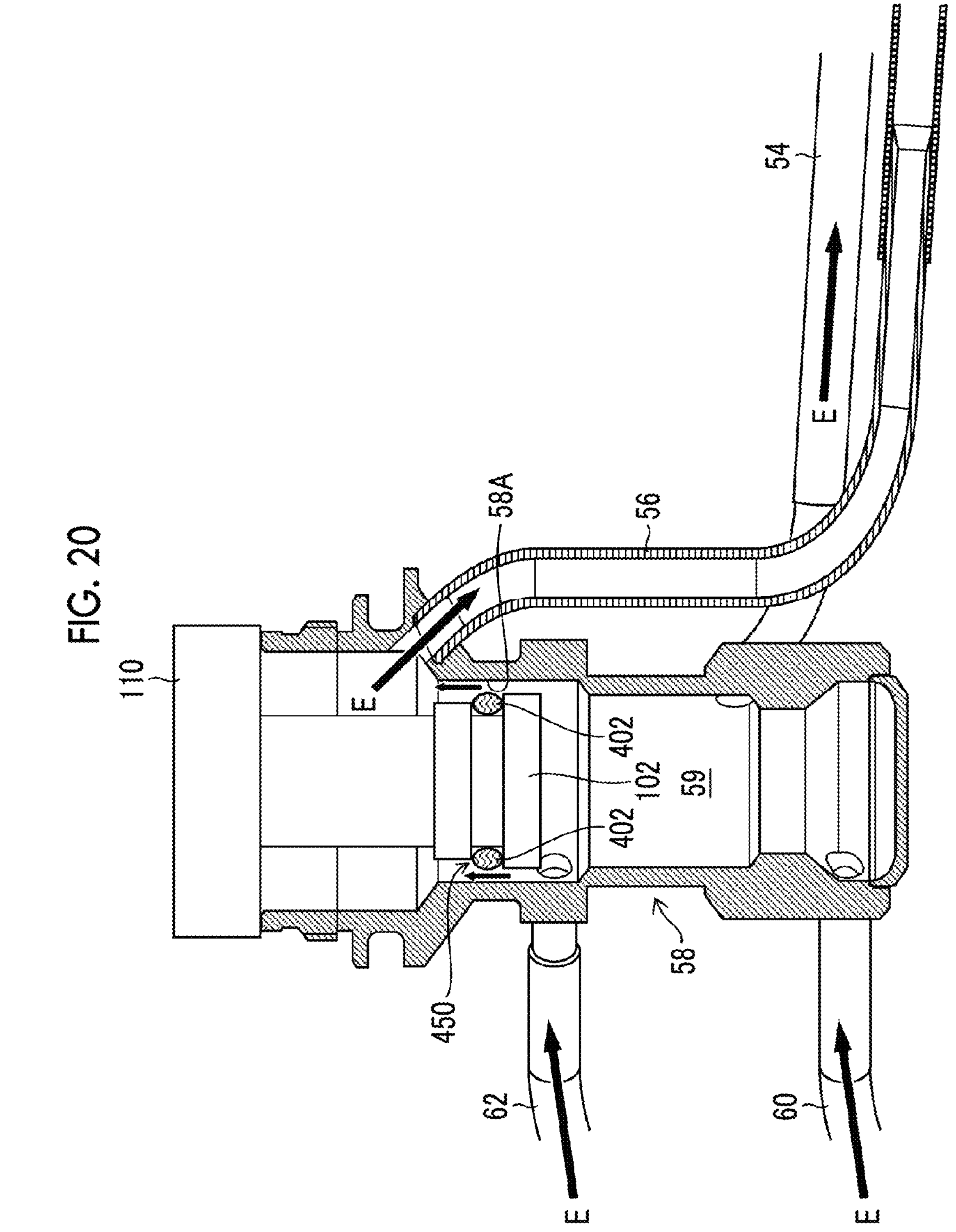
FIG. 20 is a cross-sectional view of a case in which the valve member shown in FIG. 19 is in a contact state.

FIGS. 19 and 20 are longitudinal cross-sectional views of a valve member 450 according to a fifth modification example. It should be noted that the same reference numerals are added to the same members as the members of the valve member 400 shown in FIG. 18. In addition, an arrow E shown in FIGS. 19 and 20 indicates a flow direction of the fluid 204.

The valve member 450 shown in FIGS. 19 and 20 is formed by the temperature deformable member 402 that is deformable between the contact state (see FIG. 19) and the spaced state (see FIG. 20) according to the temperature change, in the same manner as the valve member 400 shown in FIG. 18.

A difference between the form shown in FIG. 18 and the forms shown in FIGS. 19 and 20 will be described. The valve member 400 shown in FIG. 18 has a function of, in the contact state, bringing the two pipe lines (air supply pipe line 54 and air feeding pipe line 60) of the four pipe lines (air supply pipe line 54, water supply pipe line 56, air feeding pipe line 60, and water feeding pipe line 62) into a state of being out of communication with the other pipe lines (water supply pipe line 56 and water feeding pipe line 62) in the space portion 59. On the other hand, the valve member 450 shown in FIGS. 19 and 20 has a function of bringing one pipe line (water supply pipe line 56) of the four pipe lines (air supply pipe line 54, water supply pipe line 56, air feeding pipe line 60, and water feeding pipe line 62) into a state of being out of communication with the other pipe lines (air supply pipe line 54, air feeding pipe line 60, and water feeding pipe line 62) in the space portion 59 in the contact state (see FIG. 19). By applying the valve member 450 to detect the back pressure of the fluid 204 to be fed to the air supply pipe line 54 in the contact state, the clogged state of the air supply pipe line 54 can be determined. By switching the valve member 450 to the spaced state (see FIG. 20), the interior wall of the cylinder 58 including the interior wall part 58A can be washed. That is, the valve member 450 applied as the valve member according to the embodiment of the present invention need only have a function of brining at least one of the four or more pipe lines into a state of being out of communication with the other pipe lines in the space portion 59 in the contact state, and brining all of the four or more pipe lines into a state of being in communication with each other in the space portion 59 in the spaced state.

It should be noted that, although the endoscope pipe line comprising the pipe line group including the four pipe lines, and the space portion configuration member formed with the space portion communicating with the pipe line group has been described as the endoscope pipe line for determining the clogged state, the present invention is not limited to this. The present invention can also be applied to an endoscope pipe line comprising a pipe line group including four or more pipe lines and a space portion configuration member formed with a space portion communicating with the pipe line group. Such an endoscope pipe line is disclosed in, for example, JP2020-000647A. JP2020-000647A discloses an endoscope pipe line comprising a pipe line group having five pipe lines and a space portion configuration member formed with a space portion communicating with the pipe line group. Since the endoscope pipe line disclosed in JP2020-000647A is well known, the detailed description thereof will be omitted here.

[Others]

The above description is related to the clogging determination unit 202 that determines the clogged state of the branch pipe line A, but hereinafter, the clogging determination unit that determines the clogged states of a plurality of pipe lines (suction pipe line 76, cylinder 74, pipe line 72B, pipe line 72A, and forceps pipe line 72: hereinafter, referred to as a suction system pipe line C (not shown in the drawing)) constituting the suction system will be described.

Figure 21:
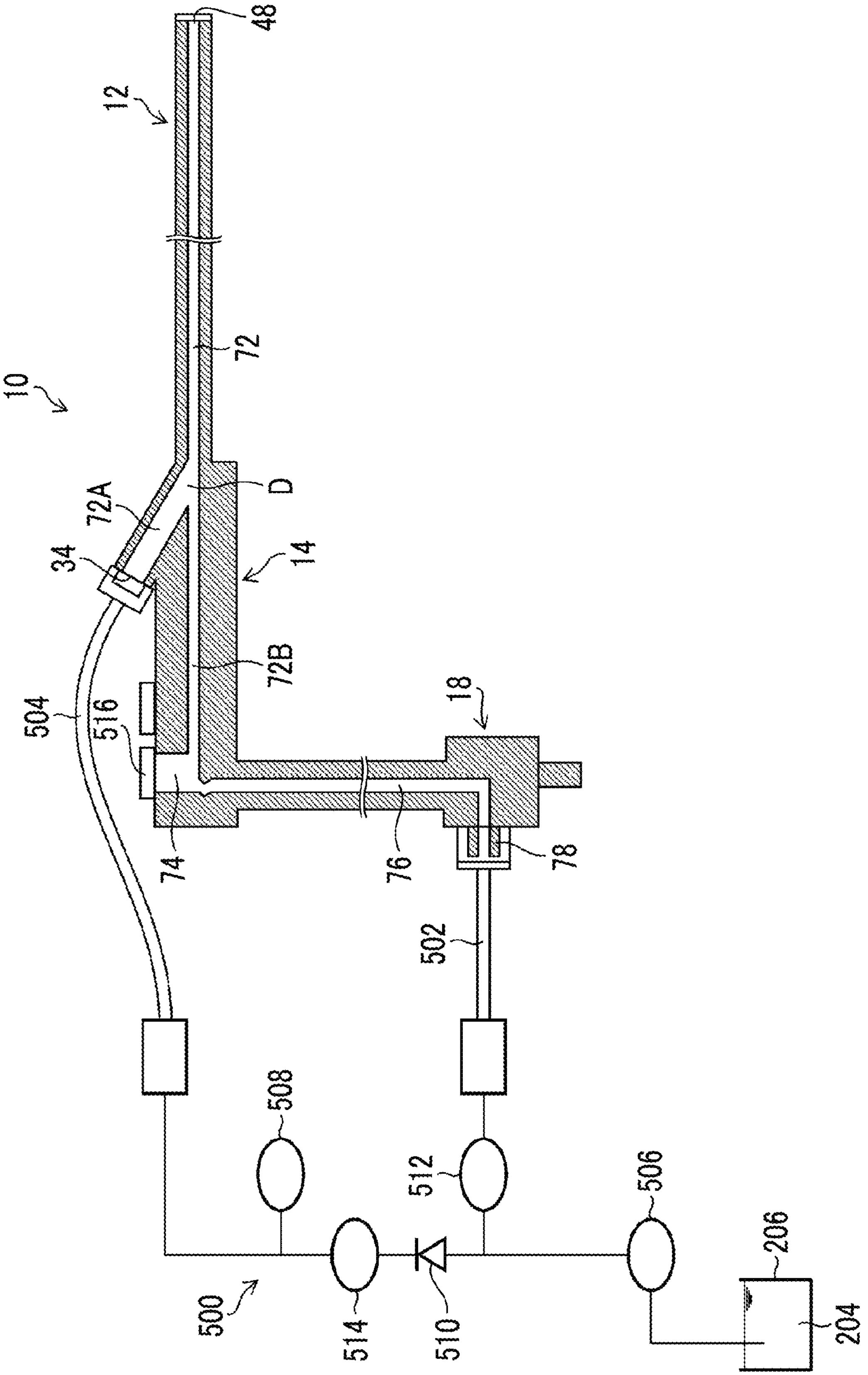
FIG. 21 is a schematic configuration diagram of a pipe line washing unit of a suction pipe line system.

FIG. 21 is a functional block diagram showing an example of a clogging determination unit 500 that performs the clogged state examination and the washing on the suction system pipe line C. It should be noted that the members that are the same as or similar to the members of the clogging determination unit 202 shown in FIG. 5 are denoted by the same reference numerals.

As shown in FIG. 21, the clogging determination unit 500 includes a fluid supply pipe line 502, a fluid drain pipe line 504, a liquid supply pump 506, a pressure sensor 508, a check valve 510, and the like. One end side of the fluid supply pipe line 502 is connected to the liquid supply pump 506 via a solenoid valve 512, and the other end side thereof is connected to the suction connector 78 of the LG connector 18. As a result, the fluid 204 stored in the tank 206 can be supplied into the suction pipe line 76 via the fluid supply pipe line 502 by the driving of the liquid supply pump 506.

One end side of the fluid drain pipe line 504 is connected to the pressure sensor 508, and the other end side thereof is connected to the forceps insertion port 34 of the hand-side operating part 14. The fluid drain pipe line 504 is connected to the check valve 510 on the downstream side of the pressure sensor 508 via a solenoid valve 514.

Next, the clogged state examination of the suction system pipe line C via the clogging determination unit 500 will be described. In this clogged state examination, the suction button 30 (see FIG. 1) is removed from the cylinder 74, and a new cap 516 is mounted in an opening portion of the cylinder 74. In this case, it is preferable to form a flow passage for leakage between the opening portion of the cylinder 74 and the cap 516, and to leak the fluid 204 from the flow passage. As a result, in the clogged state examination, an opening edge portion of the cylinder 74 can be washed.

Thereafter, the endoscope 10 is accommodated in the accommodation tank of the clogging determination device 200 (see FIG. 5), the fluid supply pipe line 502 is connected to the suction connector 78, and the fluid drain pipe line 504 is connected to the forceps insertion port 34. As a result, the preparation for the clogged state examination ends. It is also preferable to form a flow passage for leakage between the fluid supply pipe line 502 and the suction connector 78, and to leak the fluid 204 from the flow passage. Similarly, it is preferable to form a flow passage for leakage between the fluid drain pipe line 504 and the forceps insertion port 34, and to leak the fluid 204 from the flow passage. As a result, in the clogged state examination, the opening edge portion of each of the suction connector 78 and the forceps insertion port 34 can be washed. It should be noted that, in this case, the solenoid valve 512 is opened. The solenoid valve 514 is also opened. This is for removing the fluid (air and liquid) remaining in the suction system pipe line C before the back pressure is detected by the pressure sensor 508.

Next, in a case in which the clogging determination mode is executed, the liquid supply pump 506 is driven, and the fluid 204 in the tank 206 is supplied from the fluid supply pipe line 502 to the suction pipe line 76. Hereinafter, some specific examples of the clogged state examination of the suction system pipe line C will be described.

Figure 22:
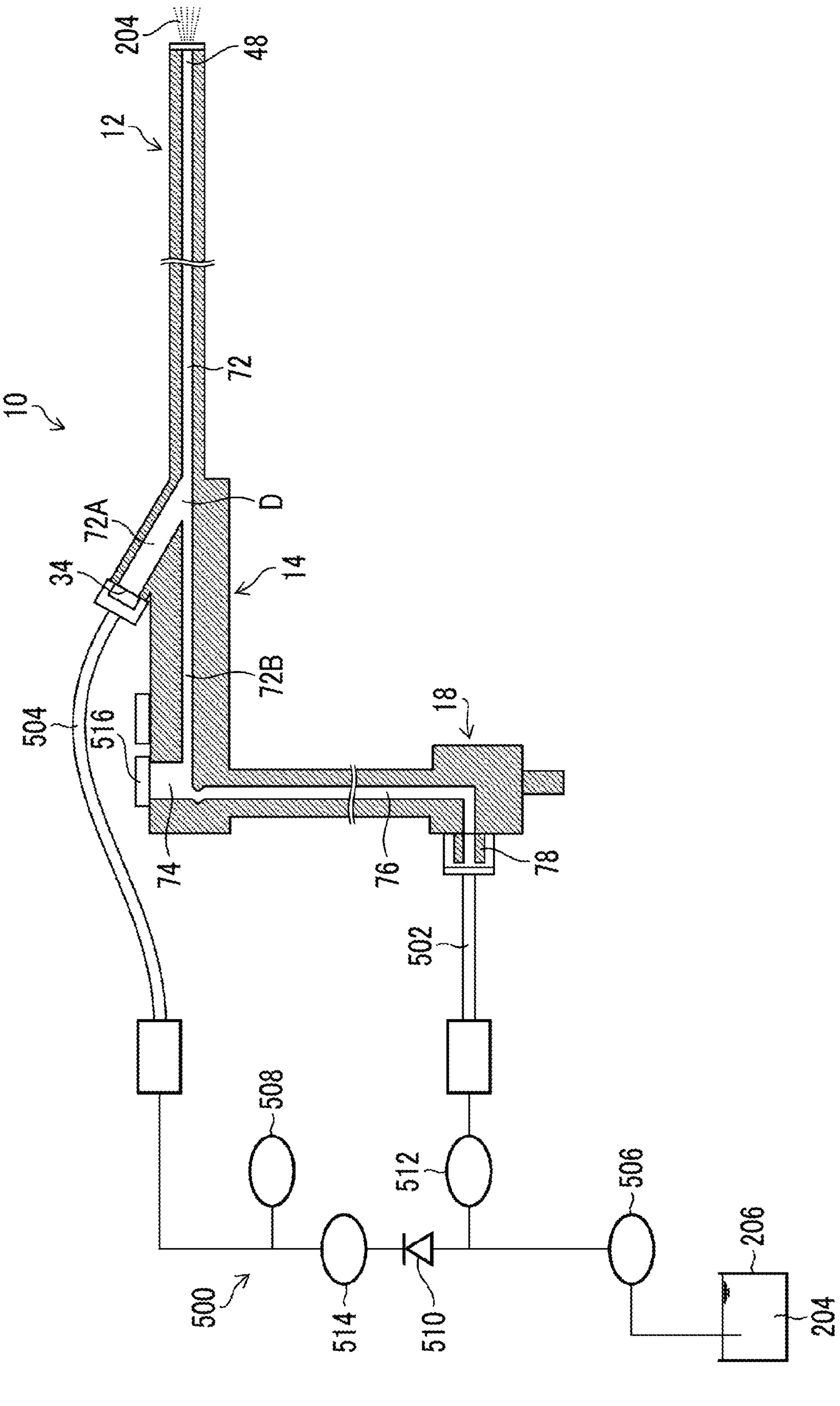
FIG. 22 is a schematic view of the branch pipe line in a case in which the pipe line is open.
Figure 23:
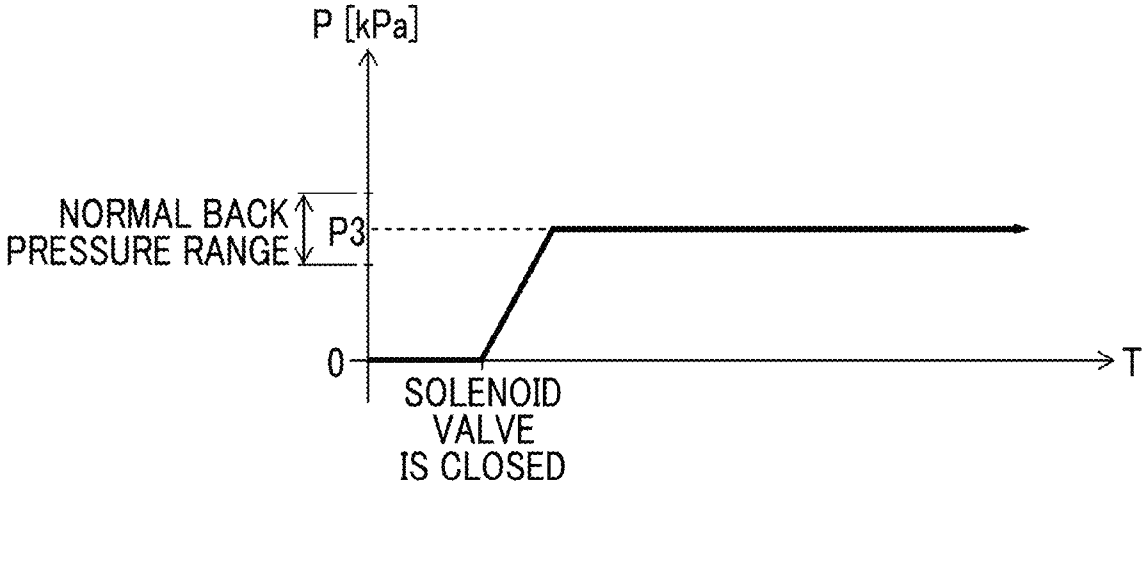
FIG. 23 is a graph showing a relationship between the examination elapsed time and the output value of the pressure sensor.

FIG. 22 schematically shows a state of the suction system pipe line C in a case in which the suction system pipe line C is open, and FIG. 23 shows a graph showing a relationship between an examination elapsed time (T) and a back pressure (P) detected by the pressure sensor 508.

As shown in FIG. 22, in a case in which the liquid supply pump 506 is driven, the fluid 204 is jetted from the forceps port 48 through the suction pipe line 76, the cylinder 74, the pipe line 72B, and the forceps pipe line 72. The surplus of the fluid 204 is fed to the fluid drain pipe line 504 from the pipe line 72B through the pipe line 72A and the forceps insertion port 34, and is drained from a drain port (not shown) of the fluid drain pipe line 504. As a result, the suction system pipe line C is filled with the fluid 204. Thereafter, the solenoid valve 514 is switched from the opened state to the closed state to stop the drainage, and the back pressure (P) after the stop is detected by the pressure sensor 508.

As shown in FIG. 23, in a case in which the solenoid valve 514 is in the closed state (solenoid valve is closed), the back pressure (P) detected by the pressure sensor 508 increases with the lapse of time, and then the back pressure reaches a certain value (P3). The example of FIG. 23 shows that the back pressure (P3) that has reached a certain value is within the normal back pressure range, and as a result, a controller (not shown) of the clogging determination unit 500 determines that the suction system pipe line C is open (that is, no clogging has occurred in the suction system pipe line C), and displays the determination result on the display unit 224 (see FIG. 5).

Figure 24:
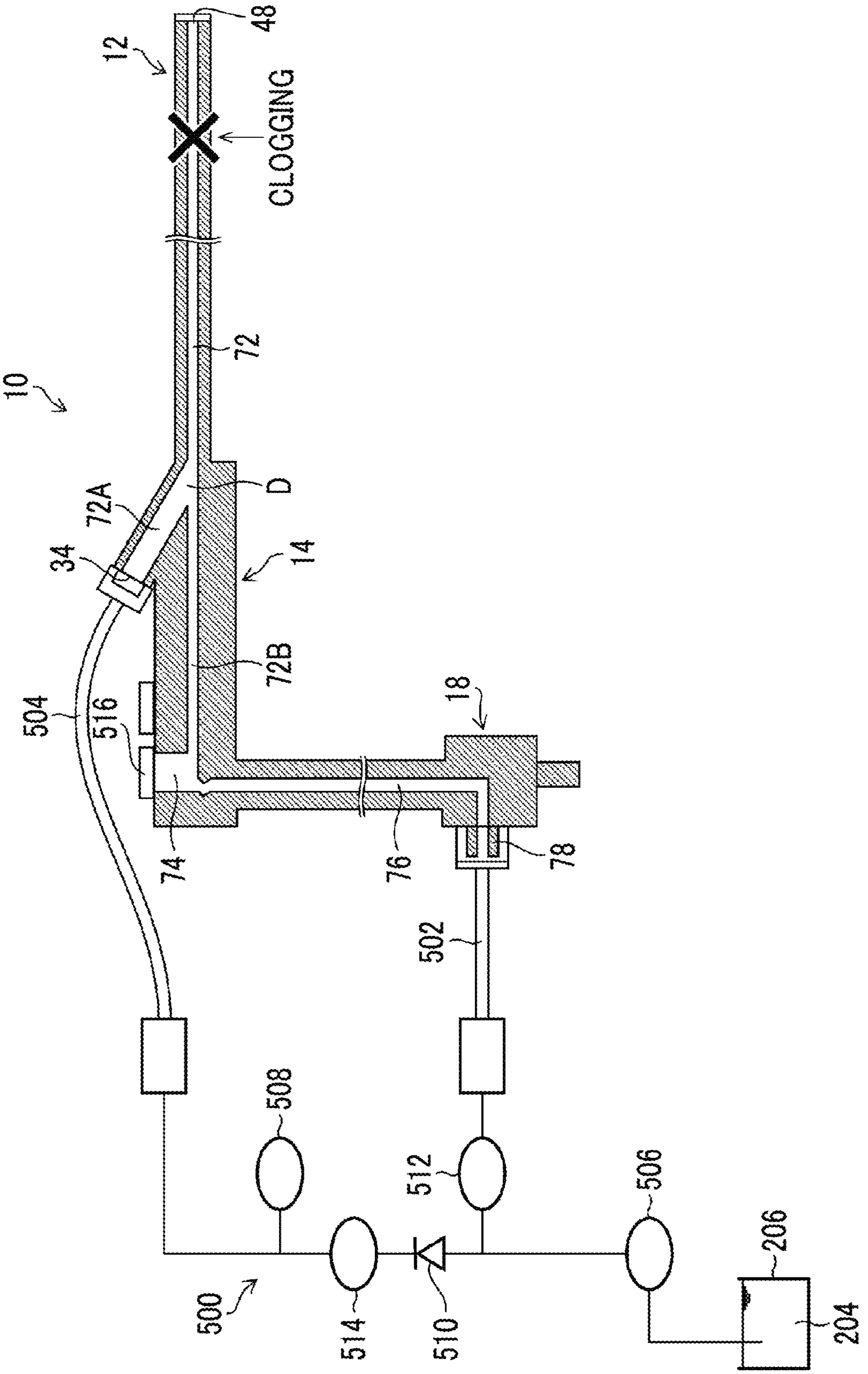
FIG. 24 is a schematic view of the branch pipe line in a case in which the clogging has occurred in the pipe line.
Figure 25:
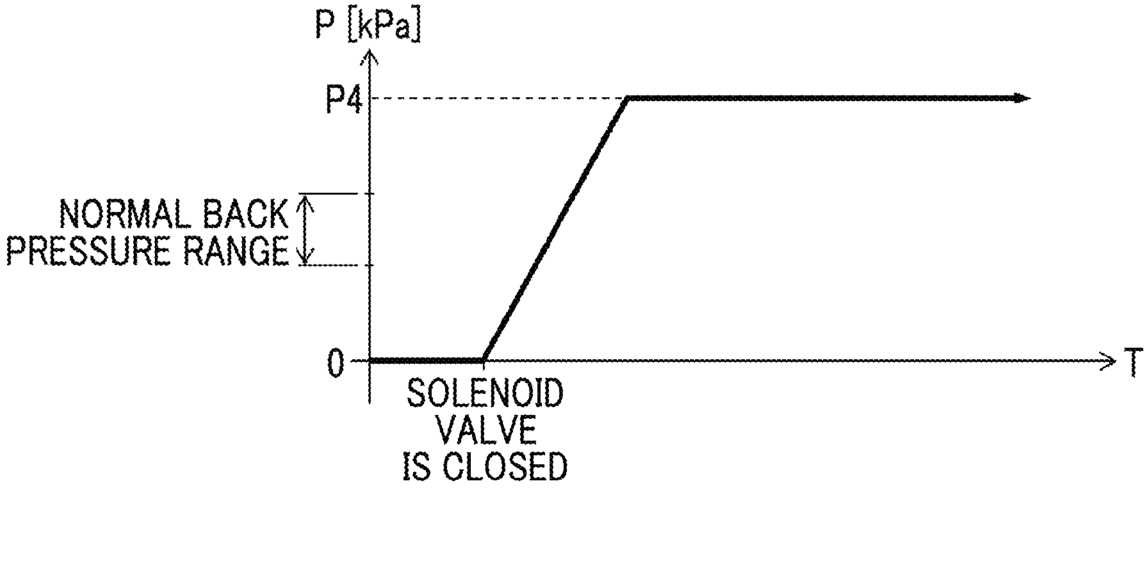
FIG. 25 is a graph showing a relationship between the examination elapsed time and the output value of the pressure sensor.

FIG. 24 schematically shows a state of the suction system pipe line C in a case in which the clogging has occurred at a position of the forceps pipe line 72 in the suction system pipe line C, and FIG. 25 shows a graph showing a relationship between the examination elapsed time (T) and the back pressure (P) detected by the pressure sensor 508.

As shown in FIG. 24, in a case in which the clogging has occurred at the position of the forceps pipe line 72 in the suction system pipe line C, as shown in FIG. 25, in a case in which the solenoid valve 514 is in the closed state (solenoid valve is closed), the back pressure detected by the pressure sensor 508 increases with the lapse of time, and then the back pressure reaches a certain value (P4). The example of FIG. 25 shows that the back pressure (P4) that has reached a certain value exceeds the normal back pressure range, and as a result, the controller (not shown) of the clogging determination unit 500 determines that the clogging has occurred in the suction system pipe line C, and displays the determination result on the display unit 224 (see FIG. 5). The controller stops the washing of the suction system pipe line C until the clogging is eliminated.

Figure 26:
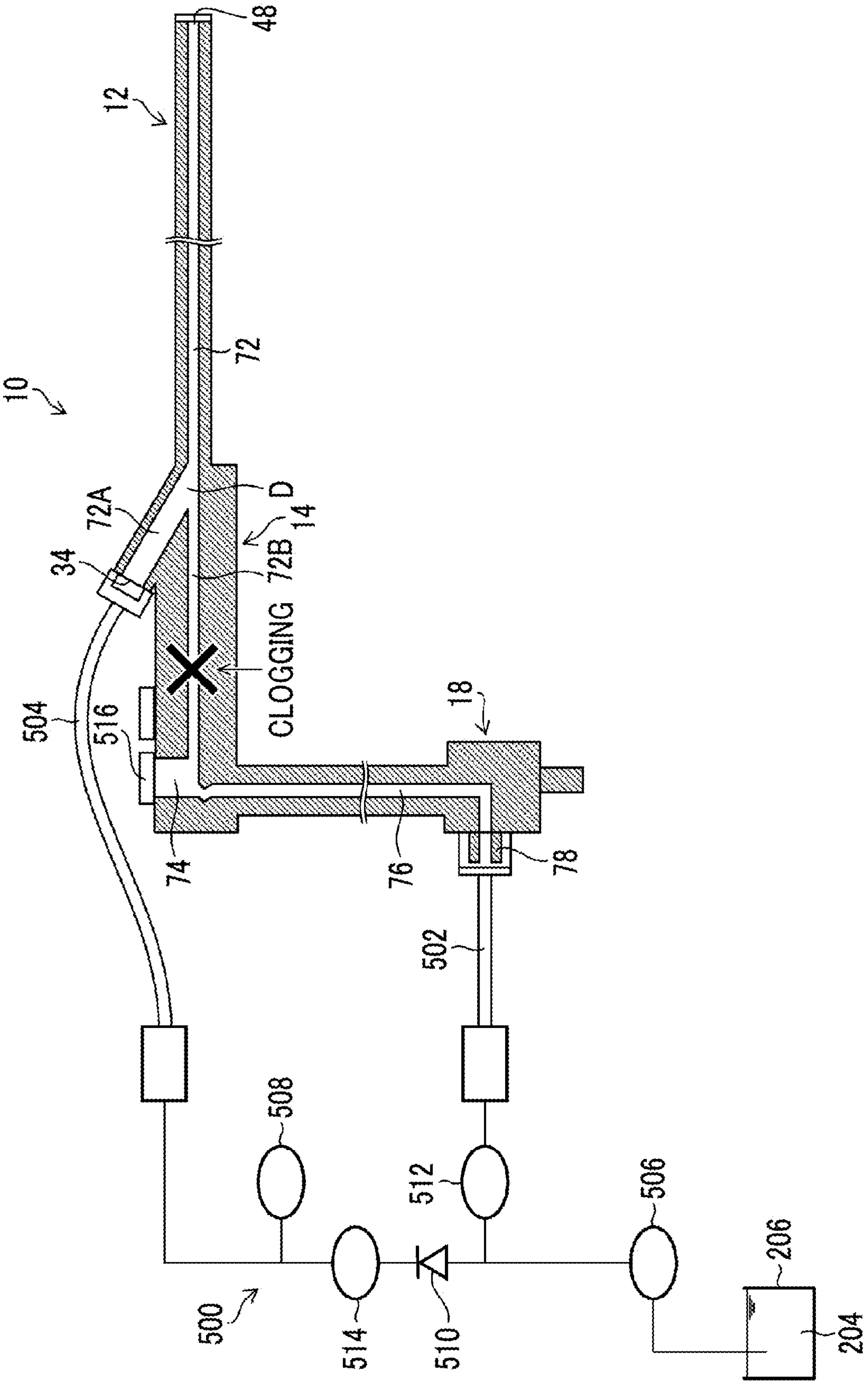
FIG. 26 is a schematic view of the branch pipe line in a case in which the clogging has occurred in the pipe line.
Figure 27:
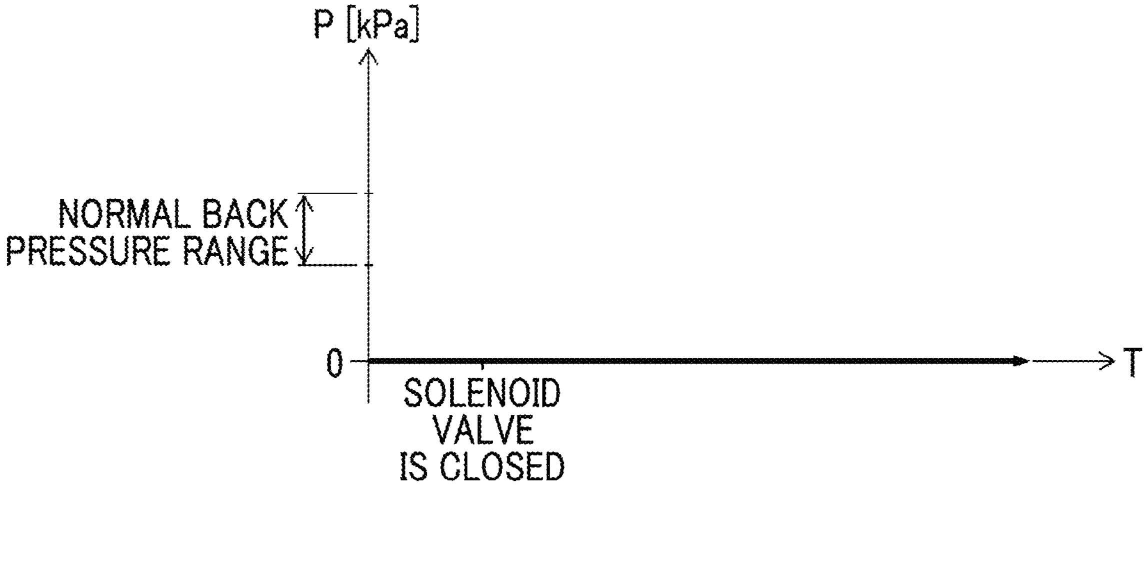
FIG. 27 is a graph showing a relationship between the examination elapsed time and the output value of the pressure sensor.

FIG. 26 schematically shows a state of the suction system pipe line C in a case in which the clogging has occurred at the position of the pipe line 72B in the suction system pipe line C, and FIG. 27 shows a graph showing a relationship between the examination elapsed time (T) and the back pressure (P) detected by the pressure sensor 508.

As shown in FIG. 26, in a case in which the clogging has occurred at the position of the pipe line 72B in the suction system pipe line C, as shown in FIG. 27, the back pressure detected by the pressure sensor 508 remains in a state of 0 (zero) even after the solenoid valve 514 is in the closed state (solenoid valve is closed). The example of FIG. 27 shows that the back pressure (zero) is less than the normal back pressure range, and as a result, the controller (not shown) of the clogging determination unit 500 determines that the clogging has occurred in the suction system pipe line C, and displays the determination result on the display unit 224 (see FIG. 5). The controller stops the washing of the suction system pipe line C until the clogging is eliminated.

Here, the suction system pipe lines C shown in FIGS. 24 and 26 are both in a state in which the clogging has occurred, but patterns of the clogging occurring in the suction system pipe line C include a first pattern in which the clogging has occurred in the pipe lines (pipe line 72A, pipe line 72B, and suction pipe line 76) on the base end side with respect to a branch part (a part in which the pipe line 72A and the pipe line 72B branch from the forceps pipe line 72, hereinafter, referred to as a branch part D) of the suction system pipe line C, and a second pattern in which the clogging has occurred in the pipe line (forceps pipe line 72) on the distal end side with respect to the branch part D. The controller determines whether the pattern of the clogging is the first pattern or the second pattern based on the back pressure detected by the pressure sensor 508, and displays the determined pattern on the display unit 224 (see FIG. 5).

Specifically, in a case in which the back pressure is the back pressure (P4) shown in the graph of FIG. 25, the back pressure exceeds the normal back pressure range, and thus it is determined that the pattern is the second pattern in which the clogging has occurred in the forceps pipe line 72 (see FIG. 24) on the distal end side with respect to the branch part D, and the fact that the pattern is the second pattern is displayed on the display unit 224 (see FIG. 5). On the other hand, in a case in which the back pressure is the back pressure (zero) shown in the graph of FIG. 27, the back pressure is less than the normal back pressure range, and thus it is determined that the pattern is the first pattern in which the clogging has occurred in at least one (in the present example, the pipe line 72B) of the pipe lines (pipe line 72A, pipe line 72B, and suction pipe line 76) on the base end side with respect to the branch part D, and the fact that the pattern is the first pattern is displayed on the display unit 224 (see FIG. 5). It should be noted that the same applies in a case in which the clogging has occurred in the pipe line 72A or the suction pipe line 76.

As described above, with the clogging determination unit 500, it is possible to detect the clogging even in a case in which the clogging has occurred in any pipe line in the suction system pipe line C. In the clogging determination unit 500, the suction system pipe line C can be washed with the fluid 204 by executing the pipe line washing mode.

Although the example of the endoscope washing device according to the embodiment of the present invention has been described above, the present invention is not limited to the above-described embodiment, and may be modified or changed in some aspects without departing from the scope of the present invention.

EXPLANATION OF REFERENCES

10: endoscope
12: insertion part
14: hand-side operating part
16: universal cable
18: LG connector
20: light source device
22: illumination window
24: pipe line
26: tube
28: air/water supply button
30: suction button
32: shutter button
34: forceps insertion port
36: distal end part
38: bendable part
40: soft part
42: distal end surface
44: observation window
46: air/water supply nozzle
48: forceps port
50: light guide rod
52: air/water supply pipe line
54: air supply pipe line
56: water supply pipe line
58: cylinder
58A: interior wall part
59: space portion
60: air feeding pipe line
62: water feeding pipe line
64: water supply connector
66: water storage tank
68: air pipe line
70: air pump
72: forceps pipe line
72A: pipe line
72B: pipe line
74: cylinder
75: space portion
76: suction pipe line
78: suction connector
80: valve member
100: washing adapter
102: shaft part
104: valve member
104A: fixing part
104B: sealing part
106: flow passage
108: flow passage
110: cap
200: clogging determination device
202: clogging determination unit
204: fluid
206: tank
208: liquid supply pump
210: electric motor
212: power supply
214: controller
216: pressure sensor
218: liquid supply pump
220: electric motor
222: power supply
224: display unit
226: pipe line
228: solenoid valve
230: liquid drain pipe line
232: solenoid valve
233: drain port
234: connection port
236: port
238: port
250: valve member
252: flexible member
252A: fixing part
254: fastener
252B: movable part
256: annular member
300: valve member
302: stepped part
304: valve body
306: spherical surface
308: spring
350: valve member
352: tapered part
400: valve member
402: temperature deformable member
404: heat transfer member
450: valve member
500: clogging determination unit
502: fluid supply pipe line
504: fluid drain pipe line
506: liquid supply pump
508: pressure sensor
510: check valve
512: solenoid valve
514: solenoid valve
516: cap
A: branch pipe line
B: branch part
C: suction system pipe line
D: branch part

What is claimed is:

1. A clogging determination device for an endoscope pipe line, the clogging determination device determining clogging of an endoscope pipe line including a pipe line group including four or more pipe lines, and a space portion configuration member formed with a space portion communicating with the pipe line group, the clogging determination device comprising:

an adapter, wherein the adapter includes a shaft part, and a valve member, configured to be switchable between a contact state and a spaced state, and a switching unit comprising at least a controller and a liquid supply pump controlled by the controller, is configured to switch the valve member between the contact state and the spaced state is provided, wherein the valve member is formed by a temperature deformable member that is deformable between the contact state and the spaced state according to a temperature change.

2. The clogging determination device for an endoscope pipe line according to claim 1, wherein the switching unit is configured to switch the valve member between the contact state and the spaced state by changing a supply condition of a fluid.

3. The clogging determination device for an endoscope pipe line according to claim 2, wherein the supply condition is a pressure or a flow rate of the fluid.

4. The clogging determination device for an endoscope pipe line according to claim 1, wherein the valve member is formed by an elastic valve.

5. The clogging determination device for an endoscope pipe line according to claim 1, the valve member is formed by a check valve.

6. The clogging determination device for an endoscope pipe line according to claim 5, wherein the valve member is a tubular flexible member that covers an outer periphery of the shaft part, a first end part of the flexible member in an axial direction of the shaft part is a fixing part that is fixed to the shaft part, and a second end part of the flexible member is a movable part that is movable along the axial direction of the shaft part, and the flexible member is decreased in diameter and is in the spaced state in a case in which the movable part is located at a restriction position at which movement in a direction away from the fixing part is restricted, and the flexible member is increased in diameter and is in the contact state in a case in which the movable part is located at a position close to the fixing part with respect to the restriction position.

7. The clogging determination device for an endoscope pipe line according to claim 5, wherein the valve member includes a valve body, and a spring that biases the valve body in a direction of abutting on the abutting target part, the valve body abuts on the abutting target part via the spring and is in the contact state, and the valve body is spaced apart from the abutting target part against a biasing force of the spring and is in the spaced state.

8. The clogging determination device for an endoscope pipe line according to claim 1, wherein the valve member has a tapered part.

9. The clogging determination device for an endoscope pipe line according to claim 1, wherein the switching unit changes a temperature of a fluid to deform the temperature deformable member between the contact state and the spaced state.

10. The clogging determination device for an endoscope pipe line according to claim 1, wherein the switching unit brings the temperature deformable member into the contact state by setting a temperature applied to the temperature deformable member to be equal to or higher than a deformable temperature at which the temperature deformable member is deformable, and brings the temperature deformable member into the spaced state by setting the temperature of the temperature deformable member to be lower than the deformable temperature.

11. A clogging determination method for an endoscope pipe line, the clogging determination method being for determining clogging of an endoscope pipe line including a pipe line group including four or more pipe lines, and a space portion configuration member formed with a space portion communicating with the pipe line group, the clogging determination method comprising:

a setting step of setting a pipe line route by switching a valve member disposed in the space portion between a contact state of being in contact with an interior wall of the space portion configuration member and a spaced state of being spaced apart from the interior wall, to perform selectively switching between a state in which at least one of the four or more pipe lines is out of communication with the other pipe lines in the space portion and a state in which all of the four or more pipe lines are in communication with each other in the space portion;

a measurement step of measuring a back pressure of a fluid by supplying the fluid into the other pipe lines;

a comparison step of comparing the measured back pressure with a clogging determination threshold value; and a determination step of determining whether or not the clogging has occurred.

12. The clogging determination method for an endoscope pipe line according to claim 11, wherein the pipe line group includes a first pipe line, a second pipe line, a third pipe line, and a fourth pipe line, and the third pipe line and the fourth pipe line are combined with each other on a side opposite to the space portion, and in the setting step, at least one of the first pipe line, the second pipe line, the third pipe line, or the fourth pipe lines is brought into a state of being out of communication with the other pipe lines in the space portion in the contact state, and all of the first to fourth pipe lines are brought into a state of being in communication with each other in the spaced state.

13. The clogging determination method for an endoscope pipe line according to claim 11, further comprising:

a filling step of filling the other pipe lines with the fluid between the setting step and the determination step.

14. The clogging determination method for an endoscope pipe line according to claim 11, wherein, in the setting step, the valve member is switched between the contact state and the spaced state by changing a pressure or a flow rate of the fluid supplied into the space portion.

15. The clogging determination method for an endoscope pipe line according to claim 11, wherein, in the setting step, the valve member is switched between the contact state and the spaced state by changing a temperature of the fluid supplied into the space portion.

* * * * *